(12) United States Patent
Takahashi et al.

(10) Patent No.: US 11,399,704 B2
(45) Date of Patent: Aug. 2, 2022

(54) VARIABLE STIFFNESS DEVICE, ENDOSCOPE, AND METHOD OF VARYING STIFFNESS OF VARIABLE STIFFNESS DEVICE

(71) Applicant: OLYMPUS CORPORATION, Tokyo (JP)

(72) Inventors: Masaya Takahashi, Hachioji (JP); Tatsuhiko Okita, Akiruno (JP)

(73) Assignee: OLYMPUS CORPORATION, Tokyo (JP)

( * ) Notice: Subject to any disclaimer, the term of this patent is extended or adjusted under 35 U.S.C. 154(b) by 407 days.

(21) Appl. No.: 16/597,923

(22) Filed: Oct. 10, 2019

(65) Prior Publication Data

US 2020/0037852 A1 Feb. 6, 2020

Related U.S. Application Data

(63) Continuation of application No. PCT/JP2017/015100, filed on Apr. 13, 2017.

(51) Int. Cl.
*A61B 1/005* (2006.01)
*A61B 1/00* (2006.01)

(52) U.S. Cl.
CPC ........ *A61B 1/0058* (2013.01); *A61B 1/00078* (2013.01)

(58) Field of Classification Search
CPC .......................... A61B 1/0058; A61B 1/00078
See application file for complete search history.

(56) References Cited

U.S. PATENT DOCUMENTS

| | | | | | |
|---|---|---|---|---|---|
| 5,055,101 | A | * | 10/1991 | McCoy | A61M 25/09 604/528 |
| 2018/0266402 | A1 | * | 9/2018 | Takahashi | F16F 1/021 |
| 2018/0321666 | A1 | * | 11/2018 | Cella | G06Q 10/04 |

FOREIGN PATENT DOCUMENTS

| | | |
|---|---|---|
| JP | H09-253032 A | 9/1997 |
| JP | 2007-54125 A | 3/2007 |
| WO | WO 2016/174741 A1 | 11/2016 |

OTHER PUBLICATIONS

English translation of International Preliminary Report on Patentability dated Oct. 24, 2019, together with the Written Opinion received in related International Application No. PCT/JP2017/015100.

(Continued)

*Primary Examiner* — Aaron B Fairchild
(74) *Attorney, Agent, or Firm* — Scully, Scott, Murphy & Presser, P.C.

(57) ABSTRACT

A variable stiffness device includes a first elongated member including high-bending stiffness portions and a low-bending stiffness portion between adjacent high-bending stiffness portions, a second elongated member arranged along the first elongated member and including shape-memory members and a connecting member between adjacent shape-memory members, a heater to heat a shape-memory member in the low-bending stiffness portion to increase the bending stiffness, and a moving mechanism to move the second elongated member relative to the first elongated member. When the heater heats a first shape-memory member in the low-bending stiffness portion, a second shape-memory member next to the first shape-memory member is arranged in a high-bending stiffness portion.

20 Claims, 11 Drawing Sheets

(56) References Cited

OTHER PUBLICATIONS

International Search Report dated Jun. 20, 2017 issued in PCT/JP2017/015100.

* cited by examiner

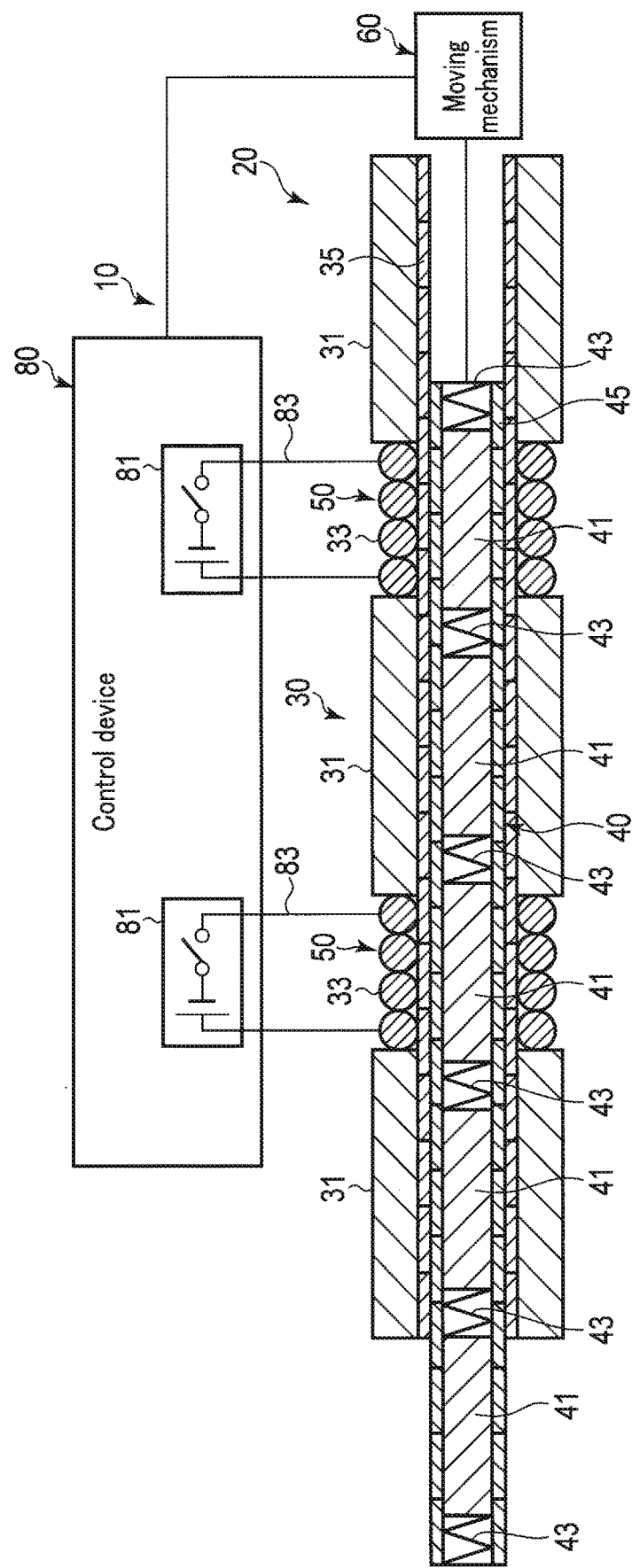
F I G. 2A

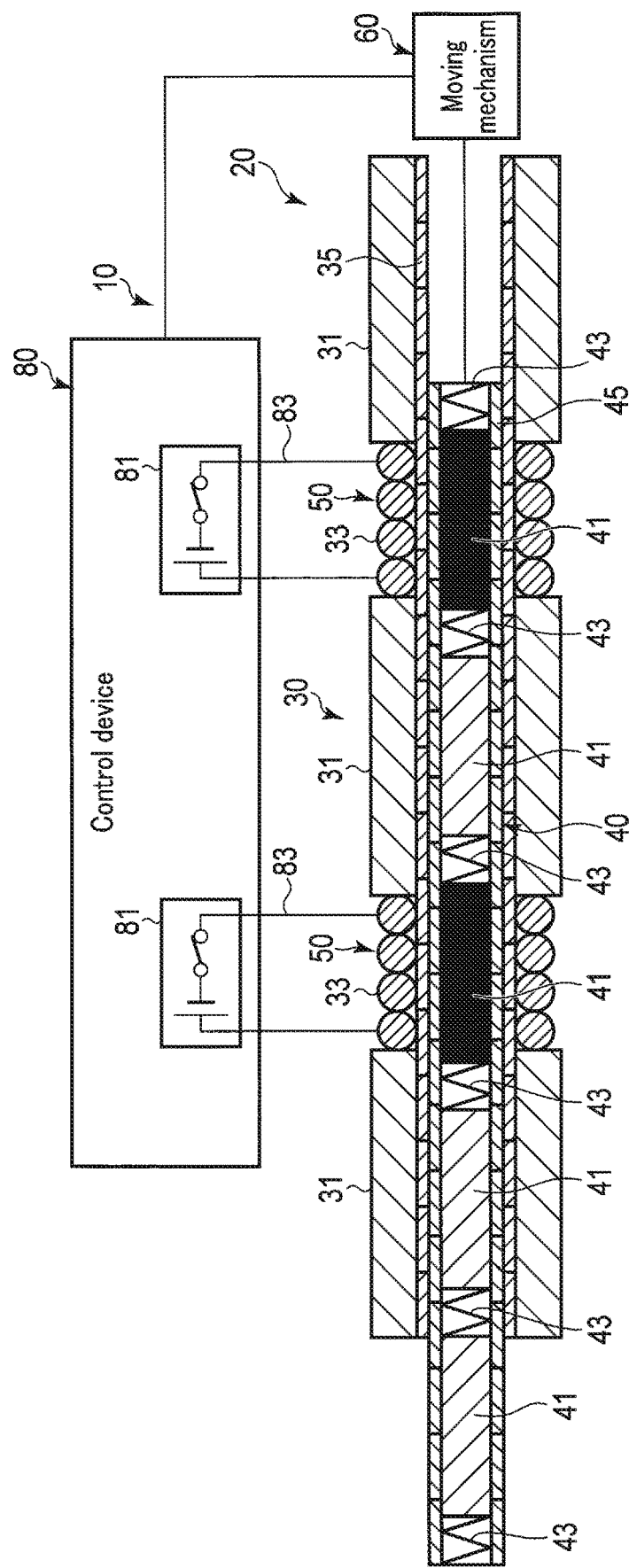
F I G. 2B

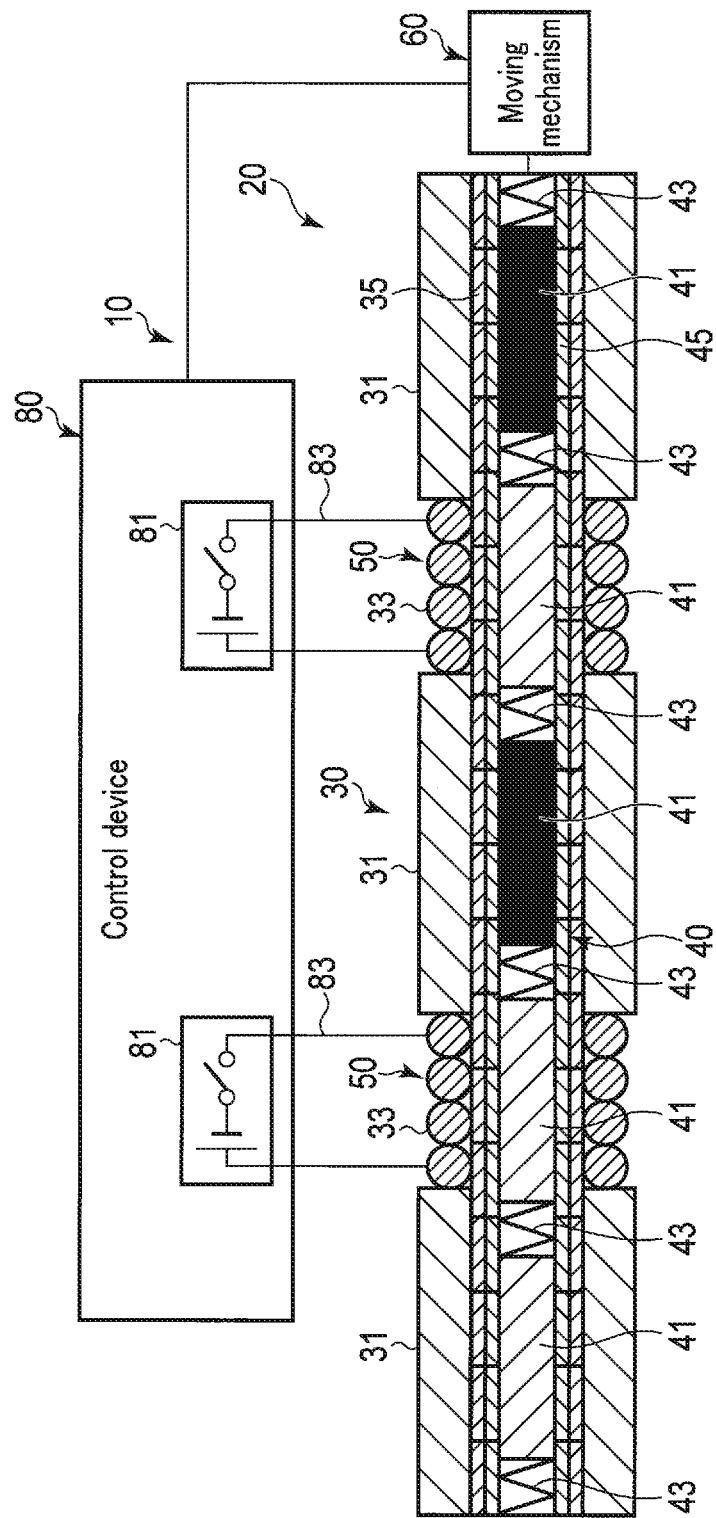
F I G. 2C

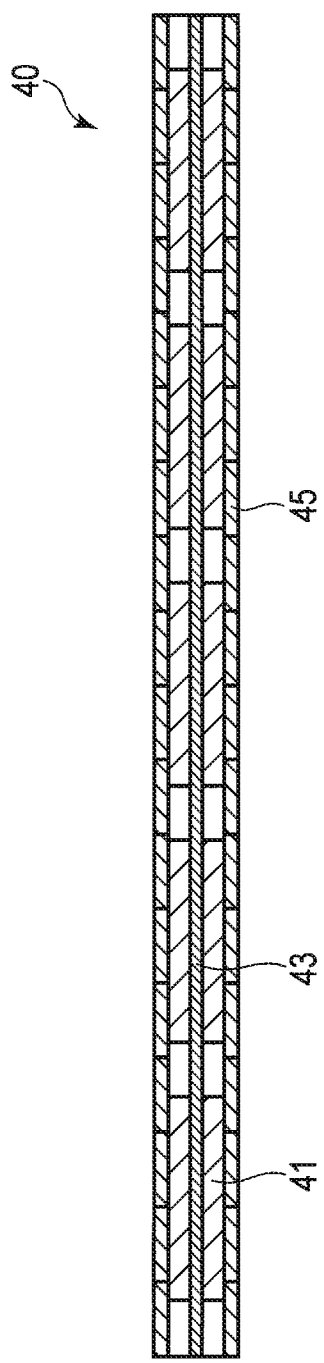

VARIABLE STIFFNESS DEVICE, ENDOSCOPE, AND METHOD OF VARYING STIFFNESS OF VARIABLE STIFFNESS DEVICE

CROSS-REFERENCE TO RELATED APPLICATIONS

This application is a Continuation Application of PCT Application No. PCT/JP2017/015100, filed Apr. 13, 2017, the entire contents of which are incorporated herein by reference.

BACKGROUND OF THE INVENTION

1. Field of the Invention

The present invention relates to a variable stiffness device configured to provide different degrees of stiffness to a flexible member, an endoscope including the variable stiffness device, and a method of varying stiffness of the variable stiffness device.

2. Description of the Related Art

International Publication No. 2016/174741, for example, discloses a variable hardness actuator for varying the hardness of a flexible member. The variable hardness actuator, installed in the flexible member, provides the flexible member with different degrees of hardness, and is both simple and durable. The variable hardness actuator includes wirings to supply currents, inducing members to generate heat in response to the currents supplied from the wirings, and a shape-memory member to which heat is transferred from the inducing members. The wirings are respectively connected to the inducing members, and the inducing members are spaced apart from each other. The shape-memory member may transition in phase from a first phase to a second phase by the heat supplied from the inducing members. When the shape-memory member is in the first phase, the shape-memory member takes a low-stiffness state, and when the shape-memory member is in the second phase, the shape-memory member takes a high-stiffness state, in which the shape-memory member has stiffness higher than that in the low-stiffness state. The variable hardness actuator provides the flexible member with a low stiffness by the shape-memory member in the low-stiffness state, and provides the flexible member with a high stiffness by the shape-memory member in the high-stiffness state. Each of the inducing members, spaced apart from each other, transfers heat to a portion of the shape-memory member in the entire length of the shape-memory member. This allows the variable hardness actuator to vary the stiffness of a desired area in the flexible member, i.e., partially vary the stiffness of the flexible member.

BRIEF SUMMARY OF THE INVENTION

A variable stiffness device according to the present invention includes: a first elongated member including high-bending stiffness portions spaced apart from each other, and at least one low-bending stiffness portion arranged between adjacent high-bending stiffness portions and having a bending stiffness lower than a bending stiffness of the high-bending stiffness portions; a second elongated member arranged along the first elongated member and including shape-memory members spaced apart from each other, and at least one connecting member arranged between adjacent shape-memory members; at least one heater configured to heat at least one of the shape-memory members that is located in the at least one low-bending stiffness portion to increase the bending stiffness of the shape-memory member; and a moving mechanism configured to move the second elongated member relative to the first elongated member. When the heater heats a first shape-memory member of the shape-memory members that is arranged in the low-bending stiffness portion to vary stiffness of the first shape-memory member, a second shape-memory member of the shape-memory members that is arranged next to the first shape-memory member to be varied in stiffness is arranged in a high-bending stiffness portion.

An endoscope according to the present invention includes a flexible member and the aforementioned variable stiffness device that is installed in the flexible member and configured to provide the flexible member with different degrees of stiffness.

A method according to the present invention of varying stiffness of the aforementioned variable stiffness device includes heating a first shape-memory member arranged in the low-bending stiffness portion to cause the first shape-memory member to transition to the second phase, and performing at least one of: maintaining a second shape-memory member arranged next to the first shape-memory member in the first phase, and cooling the second shape-memory member in the second phase.

Advantages of the invention will be set forth in the description that follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2A is a diagram showing that the variable stiffness device is in an initial state.

FIG. 2B is a diagram showing that the variable stiffness device shown in FIG. 2A has been switched from a low-stiffness state to a high-stiffness state.

FIG. 2C is a diagram showing that the variable stiffness device shown in FIG. 2B has been switched from the high-stiffness state to the low-stiffness state.

FIG. 4A is a diagram showing a first modification of a second elongated member.

DETAILED DESCRIPTION OF THE INVENTION

Hereinafter, an embodiment of the present invention will be described with reference to the drawings. In some drawings, members are partly omitted for clarification of illustration.

Figure 1A:
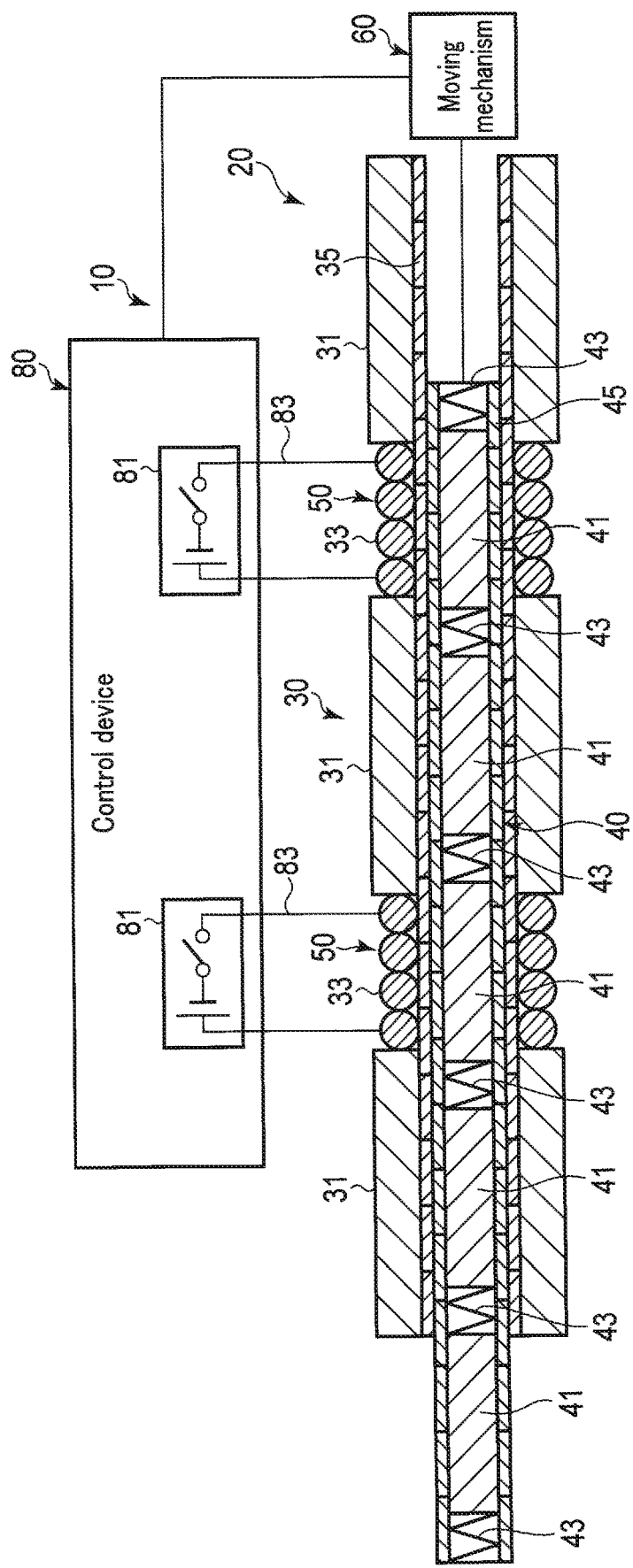
FIG. 1A is a schematic view of a variable stiffness system according to an embodiment of the present invention.
Figure 1B:
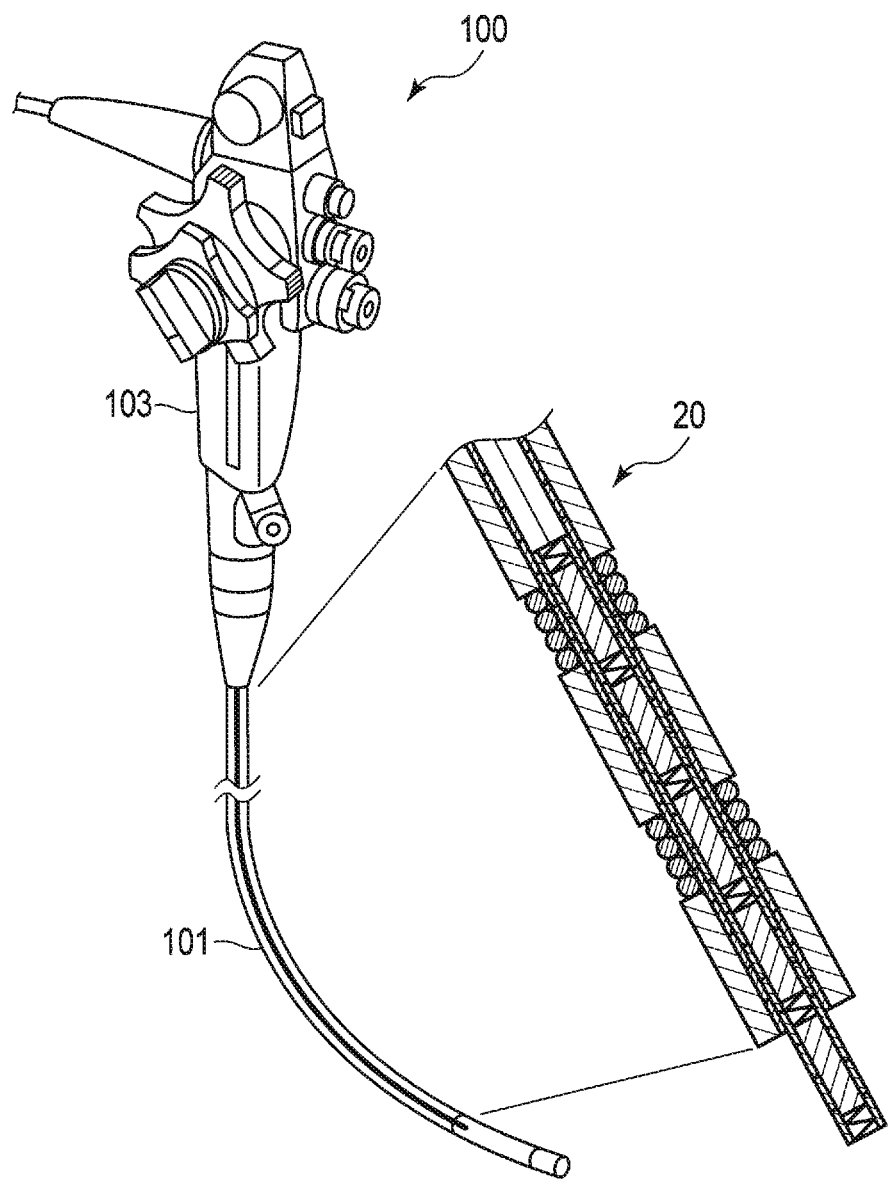
FIG. 1B is a perspective view of an endoscope incorporating a variable stiffness device of the variable stiffness system.

As shown in FIGS. 1A and 1B, a variable stiffness system 10 includes a variable stiffness device 20 to be installed in a flexible member 101, for example, and a control device 80 configured to control the variable stiffness device 20.

The variable stiffness device 20 provides the flexible member 101 with different degrees of stiffness. The variable stiffness device 20 includes a first elongated member 30 and a second elongated member 40 arranged along the first elongated member 30. The second elongated member 40 is adjacent to the first elongated member 30. The second elongated member 40 may be next to the first elongated member 30. As an example, the first elongated member 30 is an outer cylinder, and the second elongated member 40 is a core member arranged inside the first elongated member 30. As an example, the cross-sectional shape of the outer cylinder perpendicular to the longitudinal axis of the outer cylinder is annular, and the outer periphery of the cross section of the core member perpendicular to the longitudinal axis of the core member is annular. In this case, the variable stiffness device 20 provides stable stiffness against bending in any direction. The cross-sectional shapes of the outer cylinder and the core member need not necessarily be annular, and may be another shape, such as a C-shape. The first elongated member 30 and the second elongated member 40 extend over the entire length of the variable stiffness device 20. In the present embodiment, for example, the first elongated member 30 is relatively positioned and fixed to the flexible member 101, and the second elongated member 40 is movable relative to the first elongated member 30 and the flexible member 101.

The first elongated member 30 includes high-bending stiffness portions 31, which have a relatively high bending stiffness, and low-bending stiffness portions 33, which have a relatively low bending stiffness. In the present embodiment, for example, let us assume that the first elongated member 30 includes three high-bending stiffness portions 31 and two low-bending stiffness portions 33. The first elongated member 30 further includes an outer support member 35 supporting the high-bending stiffness portions 31 and the low-bending stiffness portions 33. The outer support member 35 is tubular, for example, and the second elongated member 40 is inserted into the outer support member 35, so as to be arranged inside the outer support member 35.

The outer support member 35 is a hollow member, and is, for example, cylindrical. For example, the outer support member 35 includes a coil member such as a closely-wound coil. The coil member of the outer support member 35 may be a loosely-wound coil. The outer support member 35 may be a soft tube or a tubular member in which metal wires are twisted around each other. The outer support member 35 is arranged inside the high-bending stiffness portions 31 and the low-bending stiffness portions 33, in other words, the high-bending stiffness portions 31 and the low-bending stiffness portions 33 are arranged around the outer support member 35.

Each high-bending stiffness portion 31 is a hollow member, and is tubular, for example, cylindrical. The high-bending stiffness portion 31 includes, for example, a tubular member such as a metal pipe. Examples of the metal include Steel Use Stainless (SUS). The high-bending stiffness portion 31 may further include part of the outer support member 35 covered by the tubular member. The part is a partial extent in the entire length of the outer support member 35. That is, the high-bending stiffness portion 31 may include a tubular member and part of the outer support member 35 inside the tubular member. The length of one of the high-bending stiffness portions 31 is different from the length of one of the low-bending stiffness portions 33, for example, longer than the length of one of the low-bending stiffness portions 33.

Each low-bending stiffness portion 33 is a hollow member, and is tubular, for example, cylindrical. For example, the low-bending stiffness portion 33 includes a helical coil member such as a closely-wound coil. The coil member of the low-bending stiffness portion 33 may be a loosely wound coil. The low-bending stiffness portion 33 may further include part of the outer support member 35 covered by the coil member. The part is a partial extent in the entire length of the outer support member 35. That is, the low-bending stiffness portion 33 may include a coil member and part of the outer support member 35 inside the coil member.

The tubular member of the high-bending stiffness portion 31, the coil member of the low-bending stiffness portion 33, and the coil member of the outer support member 35 are separate from one another. The low-bending stiffness portions 33 and the outer support member 35 may include a metal, wired, and helical member, for example.

The bending stiffness of the high-bending stiffness portions 31 is high, and the bending stiffness of the low-bending stiffness portions 33 is lower than the bending stiffness of the high-bending stiffness portions 31. For example, the bending stiffness of the outer support member 35 is lower than the bending stiffness of the high-bending stiffness portions 31. For example, the bending stiffness of the outer support member 35 may be substantially the same as or different from the bending stiffness of the low-bending stiffness portions 33. Thus, the first elongated member 30 is relatively easily bendable at the low-bending stiffness portions 33, and relatively hardly bendable at the high-bending stiffness portions 31. The high-bending stiffness portions 31 are cylindrical hard portions having a high bending stiffness, and the low-bending stiffness portions 33 and the outer support member 35 are cylindrical soft portions having a low bending stiffness.

The outer peripheral surface of the outer support member 35 is fixed to the inner peripheral surfaces of the high-bending stiffness portions 31 by bonding or welding, for example. The high-bending stiffness portions 31 are positioned on the outer support member 35 so as to surround the outer support member 35. The high-bending stiffness portions 31 are not in direct mechanical contact with each other in the longitudinal axis direction of the first elongated member 30, but are arranged with a desired distance from each other. In other words, the high-bending stiffness portions 31 partially surround the entire length of the outer support member 35. That is, one high-bending stiffness portion 31 does not surround the entire length of the outer support member 35, but surrounds part of the outer support member 35 in the entire length of the outer support member 35. Accordingly, spacing is provided between the high-bending stiffness portions 31 in the longitudinal axis direction of the first elongated member 30. In the present embodiment, let us assume that two spaces are provided. The high-bending stiffness portions 31 are not in direct thermal contact with each other. The longitudinal axis direction of the first elongated member 30 is the left-right direction in FIG. 1A.

Each of the low-bending stiffness portions 33 is arranged in the space between the high-bending stiffness portions 31 in the longitudinal axis direction of the first elongated member 30. Accordingly, the high-bending stiffness portions 31 and the low-bending stiffness portions 33 are alternately arranged on the outer peripheral surface of the outer support member 35 in the longitudinal axis direction of the first elongated member 30. The high-bending stiffness portions 31 and the low-bending stiffness portions 33 are arranged along the longitudinal axis direction of the first elongated member 30. The low-bending stiffness portions 33 are not in direct mechanical contact with each other, and are arranged with a desired distance from each other. The low-bending stiffness portions 33 are not in direct thermal contact with each other. An end of a low-bending stiffness portion 33 may be fixed to an end of a high-bending stiffness portion 31 adjacent thereto by bonding or welding, for example. An end of a low-bending stiffness portion 33 may be spaced apart from an end of a high-bending stiffness portion 31 adjacent thereto. Each low-bending stiffness portion 33 winds around the outer support member 35 in the space between the high-bending stiffness portions 31. In the present embodiment, one low-bending stiffness portion 33 winds not around the entire length of the outer support member 35, but around part of the outer support member 35 in the entire length of the outer support member 35. In this manner, the low-bending stiffness portions 33 partially wind around the outer support member 35. The low-bending stiffness portions 33 are positioned on the outer support member 35 by the high-bending stiffness portions 31 so as to wind around parts of the outer support member 35 in the entire length of the outer support member 35. The outer diameter of the windings of the low-bending stiffness portions 33 is substantially the same as the outer diameter of the high-bending stiffness portions 31. It is preferable that the windings of the low-bending stiffness portions 33 do not project from the high-bending stiffness portions 31 in the direction orthogonal to the longitudinal axis of the first elongated member 30. The inner peripheral surfaces of the low-bending stiffness portions 33 are in contact with the outer peripheral surface of the outer support member 35, and may be fixed to the outer peripheral surface of the outer support member 35. The inner peripheral surfaces of the low-bending stiffness portions 33 may be spaced apart from the outer peripheral surface of the outer support member 35.

Since the first elongated member 30 is relatively positioned and fixed to the flexible member 101, the low-bending stiffness portions 33 are relatively positioned and fixed to desired areas in the flexible member 101.

For example, the outer support member 35 serves as a core material of the high-bending stiffness portions 31 and the low-bending stiffness portions 33. As shown in FIG. 2C, the outer support member 35 is capable of covering the entire length of the second elongated member 40. For example, the length of the outer support member 35 is substantially the same as the length of the second elongated member 40. The length of the outer support member 35 may be longer than the length of the second elongated member 40. The outer support member 35 is interposed between the high-bending stiffness portions 31 and the low-bending stiffness portions 33, and the second elongated member 40 in the radial direction of the first elongated member 30. In this manner, the outer support member 35 is arranged on the inner peripheral side of the high-bending stiffness portions 31 and the low-bending stiffness portions 33.

The outer support member 35 is arranged in order to position the low-bending stiffness portions 33 and the high-bending stiffness portions 31, and in order to define the lengths of the high-bending stiffness portions 31 and the low-bending stiffness portions 33. The outer support member 35 is arranged for the assembly of the first elongated member 30. The outer support member 35 is arranged in order to improve the mechanical strength of the first elongated member 30. The outer support member 35 may be omitted if the low-bending stiffness portions 33 can be easily positioned relative to the high-bending stiffness portions 31.

High-bending stiffness portions 31 are arranged at the both ends of the first elongated member 30, but the disposition need not be limited thereto. Low-bending stiffness portions 33 may be arranged at the both ends, or it is also allowed that a high-bending stiffness portion 31 is arranged at an end, and a low-bending stiffness portion 33 is arranged at the other end. If members arranged at the both ends are fixed to the outer support member 35 by bonding or welding, for example, members arranged between the both ends need not be fixed to the outer support member 35.

The second elongated member 40 includes shape-memory members 41 configured to transition in phase between a first phase and a second phase, and soft members 43 softer than the shape-memory members 41. In the present embodiment, for example, let us assume that the second elongated member 40 includes five shape-memory members 41 and six soft members 43. The second elongated member 40 further includes an inner support member 45 supporting the shape-memory members 41 and the soft members 43. The inner support member 45 is tubular, for example.

When the shape-memory members 41 are in the first phase, the shape-memory members 41 take a low-stiffness state in which it is easily deformable by an external force, and exhibit a low elastic modulus. Accordingly, when the shape-memory members 41 are in the first phase, the variable stiffness device 20 provides the flexible member 101 with a relatively low stiffness by the shape-memory members 41. For example, the low stiffness is a stiffness that allows the flexible member 101 to be easily flexed. In the first phase, the first elongated member 30, the second elongated member 40, and the flexible member 101 can be easily flexed by an external force, for example.

When the shape-memory members 41 are in the second phase, the shape-memory members 41 take a high-stiffness state in which they have a stiffness higher than that in the low-stiffness state, and exhibit a high elastic modulus. Accordingly, when the shape-memory members 41 are in the second phase, the variable stiffness device 20 provides the flexible member 101 with a relatively high stiffness by the shape-memory members 41. In the high-stiffness state, the shape-memory members 41 tend to restore a shape memorized in advance against an external force. The memorized shape may be a substantially linear shape, for example. For example, the high stiffness is a stiffness that does not allow the flexible member 101 to be easily flexed, or a stiffness that allows the flexible member 101 to maintain a substantially linear state against an external force. In the second phase, for example, the first elongated member 30, the second elongated member 40, and the flexible member 101 are capable of maintaining a substantially linear state, or being gently flexed even by application of an external force as compared to the state in the first phase.

Herein, the external force means a force capable of deforming the shape-memory members 41, and gravity is considered as part of the external force.

For example, when the shape-memory members 41 are in the first phase, the bending stiffness of the shape-memory members 41 is lower than the bending stiffness of the high-bending stiffness portions 31, and is substantially the same as or lower than the bending stiffness of the low-bending stiffness portions 33. When the shape-memory members 41 are in the second phase, the bending stiffness of the shape-memory members 41 is substantially the same as or lower than the bending stiffness of the high-bending stiffness portions 31, and is higher than the bending stiffness of the low-bending stiffness portions 33. When the shape-memory members 41 are in the second phase, the bending stiffness of the shape-memory members 41 may be higher than the bending stiffness of the high-bending stiffness portions 31. The bending stiffness of the shape-memory members 41 may be either higher or lower than the bending stiffness of each of the soft members 43 and the inner support member 45, regardless of whether the shape-memory members 41 are in the first phase or in the second phase.

Each shape-memory member 41 includes a member whose phase is transformed according to the temperature, and whose stiffness is greatly varied by the transformation. Such a member has an NiTi-based shape-memory alloy wire, for example. Such a member may include a shape-memory alloy, for example. The shape-memory alloy may be an alloy containing NiTiCu, for example. The shape-memory members 41 need only be made of a material whose phase is transformed according to the temperature, and whose stiffness is varied by the transformation. Accordingly, the shape-memory members 41 may be made of materials other than a shape-memory alloy, such as a shape-memory polymer, a shape-memory gel, and a shape-memory ceramic.

The shape-memory alloy forming the shape-memory member 41 may be a shape-memory alloy that transitions in phase between the martensite phase and the austenite phase, for example. The shape-memory alloy in the martensite phase is easily plastically deformable by an external force. That is, the shape-memory alloy in the martensite phase exhibits a low elastic modulus. On the other hand, the shape-memory alloy in the austenite phase resists an external force, and is not easily deformed. Herein, let us assume that the shape-memory alloy has been deformed by a larger external force. When a large external force against the deformed shape-memory alloy is eliminated, the shape-memory alloy exhibits superelasticity and returns to its memorized shape. That is, the shape-memory alloy in the austenite phase exhibits a high elastic modulus.

The soft members 43 are bendable, for example. The soft members 43 are formed of a spring material or a rubber material, for example. For example, the soft members 43 are softer and easier to flex than the shape-memory members 41. The thermal conductivity of the soft members 43 is lower than the thermal conductivity of the shape-memory members 41.

The shape-memory members 41 and the soft members 43 are inserted into the inner support member 45, so as to be arranged inside the inner support member 45. The entire outer circumferences of the shape-memory members 41 and the soft members 43 are covered by the inner support member 45.

The shape-memory members 41 are not in direct mechanical contact with each other, and are arranged with a desired distance from each other in the longitudinal axis direction of the second elongated member 40. Accordingly, spacing is provided between the shape-memory members 41 in the longitudinal axis direction of the second elongated member 40. In the present embodiment, let us assume that four spaces are provided. The shape-memory members 41 are not in direct thermal contact with each other. The longitudinal axis direction of the second elongated member 40 is the left-right direction in FIG. 1A, and is the same as the longitudinal axis direction of the first elongated member 30.

Each soft member 43 is arranged in the space between the shape-memory members 41 in the longitudinal axis direction of the second elongated member 40. Accordingly, the shape-memory members 41 and the soft members 43 are alternately arranged inside the inner support member 45 in the longitudinal axis direction of the second elongated member 40. The shape-memory members 41 and the soft members 43 are arranged along the longitudinal axis direction of the second elongated member 40. The soft members 43 are not in direct mechanical contact with each other, and are arranged with a desired distance from each other. The soft members 43 are not in direct thermal contact with each other. The soft members 43 arranged between the shape-memory members 41 are arranged for positioning of the shape-memory members 41. Ends of the soft member 43 are in contact with ends of the shape-memory members 41 adjacent thereto. The ends of the soft member 43 may be fixed to the ends of the shape-memory members 41 adjacent thereto by bonding or welding, for example.

In the present embodiment, for example, soft members 43 are arranged at both ends of the second elongated member 40. The outer peripheral surfaces of the soft members 43 arranged at both ends are fixed to the inner peripheral surface of the inner support member 45 by bonding or welding, for example. Thereby, soft members 43 and shape-memory members 41 other than those arranged at both ends are positioned relative to the inner support member 45 without being fixed to the inner support member 45. Of course, it is also allowed that the outer peripheral surfaces of the shape-memory members 41 and the soft members 43 are fixed to the inner peripheral surface of the inner support member 45 by bonding or welding, for example, so that the shape-memory members 41 and the soft members 43 are respectively positioned. The soft members 43 may be omitted if the shape-memory members 41 are fixed to the inner support member 45 by bonding or welding, for example.

Soft members 43 are arranged at the both ends of the second elongated member 40, but the disposition need not be limited thereto. Shape-memory members 41 may be arranged at the both ends, or it is also allowed that a soft member 43 is arranged at an end and a shape-memory 41 is arranged at the other end. If members arranged at the both ends are fixed to the inner support member 45 by bonding or welding, for example, members arranged between the both ends need not be fixed to the inner support member 45.

The inner support member 45 is a hollow member, and is tubular cylindrical, for example. The inner support member 45 is arranged on the outer peripheral side of the shape-memory members 41 and the soft members 43. For example, the inner support member 45 includes a coil member such as a closely-wound coil. The coil member of the inner support member 45 may be a loosely-wound coil. The inner support member 45 may be a soft tube or a tubular member in which metal wires are twisted around each other. The inner support member 45 may include a metal, wired, and helical member, for example. For example, the bending stiffness of the inner support member 45 is substantially the same as the bending stiffness of the soft members 43.

The outer peripheral surface of the inner support member 45 is in contact with the inner peripheral surface of the outer support member 35, and the inner support member 45 is slid on the outer support member 35 by a moving mechanism 60, which will be described later. Since the shape-memory members 41 and the soft members 43 are fixed to the inner support member 45, the shape-memory members 41 and the soft members 43 move together with the inner support member 45 in association with the movement of the inner support member 45. If the inner support member 45 is movable relative to the outer support member 35, it is also allowed that the outer peripheral surface of the inner support member 45 does not contact the inner peripheral surface of the outer support member 35, so that spacing is formed between the outer peripheral surface of the inner support member 45 and the inner peripheral surface of the outer support member 35.

The entire length of the inner support member 45, inserted into the outer support member 35, can be covered by the outer support member 35. For example, the length of the inner support member 45 is substantially the same as the length of the outer support member 35. The length of the inner support member 45 may be smaller than the length of the outer support member 35. The shape-memory members 41 and the soft members 43 are inserted into the inner support member 45, so that the inner support member 45 is arranged outside the shape-memory members 41 and the soft members 43. The inner support member 45 serves as a protection member that protects the outer peripheral surfaces of the shape-memory members 41 and the soft members 43 against the inner peripheral surface of the outer support member 35. The inner support member 45 is an interposed member that is interposed between the outer support member 35, and the shape-memory members 41 and the soft members 43, so as to prevent the outer support member 35 from coming into direct contact with the shape-memory members 41 and the soft members 43.

The inner support member 45 is arranged in order to position the shape-memory members 41 and the soft members 43, and in order to define the lengths of the shape-memory members 41 and the soft members 43. The inner support member 45 is arranged for the assembly of the second elongated member 40. The inner support member 45 is arranged in order to improve the mechanical strength of the second elongated member 40.

The length of one of the high-bending stiffness portions 31 is longer than the length of one of the shape-memory members 41, and longer than the length of one of the soft members 43. Accordingly, the high-bending stiffness portion 31 winds around the entire length of one of the shape-memory members 41 and the entire length of one of the soft members 43 through the outer support member 35 and the inner support member 45. The length of one of the low-bending stiffness portions 33 is smaller than the length of one of the shape-memory members 41, and longer than the length of one of the soft members 43. Accordingly, the low-bending stiffness portion 33 winds around the majority of the entire length of one of the shape-memory members 41 through the outer support member 35 and the inner support member 45. The length of one of the shape-memory members 41 is longer than the length of one of the soft members 43. The sum of the length of one of the high-bending stiffness portions 31 and the length of one of the low-bending stiffness portions 33 is longer than twice the length of one of the shape-memory members 41.

In the present embodiment, in the state in which the first elongated member 30 is inserted into the second elongated member 40, the shape-memory members 41 overlap the high-bending stiffness portions 31 or the low-bending stiffness portions 33, and the soft members 43 overlap the high-bending stiffness portions 31.

For example, the overlap with the high-bending stiffness portions 31 means that the second and fourth shape-memory members 41 from the left shown in FIG. 1A are arranged in the high-bending stiffness portions 31, and the second and fourth shape-memory members 41 from the left shown in FIG. 1A are adjacent to the high-bending stiffness portions 31 through the outer support member 35 and the inner support member 45. At this time, for example, the entire lengths of the second and fourth shape-memory members 41 from the left shown in FIG. 1A are covered by the high-bending stiffness portions 31 through the outer support member 35 and the inner support member 45, and the entire lengths of the second and fourth shape-memory members 41 from the left shown in FIG. 1A are arranged inside the high-bending stiffness portions 31 through the outer support member 35 and the inner support member 45, and are contained in the high-bending stiffness portions 31. The above description has been made using the second and fourth shape-memory members 41 from the left shown in FIG. 1A; however, the same applies to the soft members 43.

For example, the overlap with the low-bending stiffness portions 33 means that the third and fifth shape-memory members 41 from the left shown in FIG. 1A are arranged in the low-bending stiffness portions 33, and the third and fifth shape-memory members 41 from the left shown in FIG. 1A are adjacent to the low-bending stiffness portions 33 through the outer support member 35 and the inner support member 45. At this time, for example, the majority of the entire length of the third and fifth shape-memory members 41 from the left shown in FIG. 1A is covered by the low-bending stiffness portions 33 through the outer support member 35 and the inner support member 45, and the majority of the entire length of the third and fifth shape-memory members 41 from the left shown in FIG. 1A is arranged inside the low-bending stiffness portions 33 through the outer support member 35 and the inner support member 45, and is contained in the low-bending stiffness portions 33.

In this manner, the shape-memory members 41 (see the second and fourth shape-memory members 41 from the left shown in FIG. 1A) that are arranged next to the shape-memory members 41 (see the third and fifth shape-memory members 41 from the left shown in FIG. 1A) that are arranged in the low-bending stiffness portions 33 are arranged in the high-bending stiffness portions 31.

The variable stiffness device 20 includes inducing members 50 and a moving mechanism 60 configured to move the second elongated member 40 relative to the first elongated member 30.

The inducing members 50 have the property of generating heat in response to current supply from the control device 80. The inducing members 50 transfer the generated heat to the shape-memory members 41 arranged in the inducing members 50. Thereafter, the inducing members 50 cause the shape-memory members 41 to induce transition in phase between the first phase and the second phase. One of the inducing members 50 causes the corresponding shape-memory member 41 to vary the stiffness of part of the second elongated member 40 in the longitudinal axis direction of the second elongated member 40. The inducing members 50 may be arranged at positions where the shape-memory members 41 can transition in phase.

The present embodiment is an example of a configuration in which the low-bending stiffness portions 33 include the inducing members 50, and the low-bending stiffness portions 33 also serve as the inducing members 50. For example, when the low-bending stiffness portions 33 also serve as the inducing members 50, the configuration of the variable stiffness device 20 can be simplified.

When the low-bending stiffness portions 33 also serve as the inducing members 50, the low-bending stiffness portions 33 include a conductive material. For example, the low-bending stiffness portions 33 may be made of a heating wire, i.e., a conductive member with a large electric resistance. The low-bending stiffness portions 33 are coiled. For example, a first insulating film (not illustrated) is arranged around the low-bending stiffness portions 33. The first insulating film prevents a short circuit between the low-bending stiffness portions 33 and the outer support member 35 and a short circuit between the high-bending stiffness portions 31 and the low-bending stiffness portions 33.

For example, a second insulating film (not illustrated) is arranged around the outer support member 35. The second insulating film prevents a short circuit between the low-bending stiffness portion 33 and the outer support member 35, a short circuit between the high-bending stiffness portion 31 and the outer support member 35, and a short circuit between the outer support member 35 and the inner support member 45.

Here, transition in phase of the shape-memory members 41 by heat will be described.

The control device 80 includes drivers 81 configured to independently drive the low-bending stiffness portions 33, respectively. Each driver 81 includes a power supply and a switch. Each driver 81 is electrically connected to the corresponding low-bending stiffness portion 33 through wirings 83. For example, the wiring 83 is a metal wired member. The wirings 83 need only be electrically connected to the low-bending stiffness portion 33, and may be either integral with or separate from the low-bending stiffness portion 33. Each driver 81 supplies a current to the corresponding low-bending stiffness portion 33 through the wirings 83 in response to an ON operation on the switch, and stops supplying the current to the low-bending stiffness portion 33 in response to an OFF operation on the switch.

The low-bending stiffness portions 33 have the property of generating heat in response to the current supply from the control device 80. The calorific value of the low-bending stiffness portions 33 depends on the amount of current supplied. The low-bending stiffness portions 33 serve as inducing members 50 configured to cause the shape-memory members 41 to transition in phase between the first phase and the second phase. Specifically, the low-bending stiffness portions 33 serve as coil heaters, which are heating portions configured to heat the shape-memory members 41 through the outer support member 35 and the inner support member 45. The shape-memory members 41 have the property of transitioning in phase from the first phase to the second phase by the heat generated from the low-bending stiffness portions 33, which serve as the inducing members 50. Specifically, the low-bending stiffness portion 33, which serves as the inducing member 50, causes a shape-memory member 41 that is arranged in the low-bending stiffness portions 33 by the moving mechanism 60 to transition in phase between the first phase and the second phase. Thereafter, the low-bending stiffness portion 33 varies the stiffness state of the shape-memory member 41, thereby varying the stiffness of part of the second elongated member 40 in the longitudinal axis direction of the second elongated member 40.

Specifically, in the present embodiment, one low-bending stiffness portion 33 winds around part of the outer support member 35 in the entire length of the outer support member 35. Accordingly, one low-bending stiffness portion 33 does not heat the entire length of the outer support member 35, but heats part of the outer support member 35 in the entire length of the outer support member 35; in other words, partially heats the outer support member 35. The low-bending stiffness portions 33 may heat also the periphery of the part of the outer support member 35 as well as the part. The heat is transferred from the part of the outer support member 35 to part of the inner support member 45 in the entire length of the inner support member 45 that is wound by the part of the outer support member 35. The heat is transferred from the part of the inner support member 45 to a shape-memory member 41 that is wound by the part of the inner support member 45. The shape-memory member 41 is heated over substantially the entire length of the shape-memory member 41. That is, one low-bending stiffness portion 33 heats one shape-memory member 41 that substantially overlaps the entire length of the low-bending stiffness portion 33 through the outer support member 35 and the inner support member 45. In other words, a low-bending stiffness portion 33 that has generated heat heats only a shape-memory member 41 that overlaps the low-bending stiffness portions 33 that have generated the heat.

The low-bending stiffness portion 33 varies the stiffness of a shape-memory member 41 that is selected from among all the shape-memory members 41; in other words, heats a desired area in the second elongated member 40. In this manner, the low-bending stiffness portions 33 partially heat the second elongated member 40.

When the shape-memory member 41 is in the first phase because the shape-memory member 41 is not heated or the shape-memory member 41 has been cooled, the shape-memory member 41 is in the low-stiffness state, so as to be a soft portion. When the shape-memory member 41 is in the second phase because the shape-memory member 41 has been heated, the shape-memory member 41 is in the high-stiffness state, so as to be a hard portion.

The heat transfer range in the shape-memory members 41 is adjusted according to, for example: the temperature of the heat; the length and the thickness of each of the high-bending stiffness portions 31, the low-bending stiffness portions 33, the outer support member 35, and the inner support member 45; the thermal conductivity of each of the high-bending stiffness portions 31, the outer support member 35, the shape-memory members 41, and the inner support member 45; and the material of each of the high-bending stiffness portions 31, the low-bending stiffness portions 33, the outer support member 35, the shape-memory members 41, and the inner support member 45. The length of the heat transfer range in the shape-memory members 41 means the length of the second elongated member 40 in the longitudinal axis direction.

The shape-memory members 41 have a slim exterior shape. The low-bending stiffness portions 33, each of which includes a wired member, are arranged around the inner support member 45 and the outer support member 35, which are arranged around the shape-memory members 41. The low-bending stiffness portions 33 are arranged with a desired distance from each other along the longitudinal axis direction of the variable stiffness device 20, which is the left-right direction in FIG. 1A. The low-bending stiffness portions 33 spirally extend around the outer support member 35. With such a configuration, the heat generated from the low-bending stiffness portions 33 is efficiently transferred only to the shape-memory members 41 overlapping the low-bending stiffness portions 33 through the outer support member 35 and the inner support member 45.

The thermal conductivity of the soft members 43 is lower than the thermal conductivity of the shape-memory members 41. This suppresses heat transfer from a heated shape-memory member 41 to another, non-heated shape-memory member 41 through the soft members 43.

For example, the heat transfer from the low-bending stiffness portions 33 to the high-bending stiffness portions 31, and the heat transfer from the high-bending stiffness portions 31 to the inner support member 45 through the outer support member 35 are suppressed by the thermal conductivities of the high-bending stiffness portions 31, the outer support member 35, and the inner support member 45. For example, this suppression suppresses heat transfer from the first low-bending stiffness portion 33 from the left shown in FIG. 1A to the shape-memory members 41 other than the third shape-memory member 41 from the left shown in FIG. 1A, which overlaps the first low-bending stiffness portion 33 from the left shown in FIG. 1A, (see, for example, the first, second, fourth, and fifth shape-memory members 41 from the left shown in FIG. 1A) through the high-bending stiffness portions 31, the outer support member 35, and the inner support member 45.

Although not illustrated, the first elongated member 30 may include heat insulating members arranged between the high-bending stiffness portions 31 and the low-bending stiffness portions 33 in the longitudinal axis direction of the first elongated member 30. For example, the heat insulating members are fixed to ends of the high-bending stiffness portions 31, and are ring-shaped. Each low-bending stiffness portion 33 is sandwiched between two heat insulating members in the longitudinal axis direction of the first elongated member 30. The heat insulating members are fixed to ends of the low-bending stiffness portions 33, so as to be thermally connected to the low-bending stiffness portions 33. The heat insulating member prevents the heat generated from the low-bending stiffness portions 33 from being transferred to the high-bending stiffness portions 31. For example, the heat insulating member is a member having a low thermal conductivity, such as a resin.

For example, heat transfer from the first low-bending stiffness portion 33 from the left shown in FIG. 1A to the shape-memory members 41 other than the third shape-memory member 41 from the left shown in FIG. 1A, which overlaps the first low-bending stiffness portion 33 from the left shown in FIG. 1A, (see, for example, the first, second, fourth, and fifth shape-memory members 41 from the left shown in FIG. 1A) through the outer support member 35, the inner support member 45, and the soft member 43 is suppressed by the thermal conductivities of the outer support member 35, the inner support member 45, and the soft member 43.

In this manner, the shape-memory member 41 that has generated the heat is prevented from heating shape-memory members 41 other than the shape-memory member 41 that overlaps that low-bending stiffness portions 33.

The low-bending stiffness portions 33 may have the same structure. However, the configuration is not limited thereto, and the low-bending stiffness portions 33 may include different structures. For example, the different structures may have different lengths, thicknesses, and pitches, and may be made of different materials. That is, all or some of the low-bending stiffness portions 33 may have the same or different characteristics.

For example, the moving mechanism 60 moves the second elongated member 40 relative to the first elongated member 30. In the present embodiment, the second elongated member 40 is movable along the first elongated member 30 by the moving mechanism 60. The outer peripheral surface of the inner support member 45 slides on the inner peripheral surface of the outer support member 35. For example, the moving mechanism 60 moves the second elongated member 40 by pulling or pushing the second elongated member 40. For example, the inner support member 45 is pulled or pushed. The shape-memory members 41 and the soft members 43 move in accordance with the movement of the second elongated member 40. The moving mechanism 60 is electrically connected to the control device 80, and the movement is controlled by the control device 80.

For example, the moving mechanism 60 includes a motor (not illustrated) and a moving member (not illustrated) connected to an end of the second elongated member 40 and configured to move the second elongated member 40 by the rotational force of the motor. The motor may be arranged in the control section 103 (see FIG. 1B) connected to the proximal portion of an insertion section (to be described later), which serves as the flexible member 101. For example, the motor may be driven by an ON/OFF operation of a switch in the control section 103. For example, the moving member is directly connected to an end of the inner support member 45, and pulls or pushes the second elongated member 40 by a rotational force. The moving member extends from the position where the motor is arranged to the end of the inner support member 45. For example, the moving member is arranged inside the control section 103 and the flexible member 101. For example, the moving member is a wired member.

The control device 80 is configured by a hardware circuit including an ASIC, for example. The control device 80 may be configured by a processor. When the control device 80 is configured by a processor, a program code for causing the processor to serve as the control device 80 by being executed by the processor is stored in an internal memory of the processor or an external memory (not illustrated) arranged so as to be accessible by the processor. For example, the control device 80 may be arranged in the control section 103. The control device 80 controls the pulling, pushing, and deactivation of the moving mechanism 60 in accordance with the operation on the switch.

Hereinafter, the relationship between the variable stiffness device 20 and the flexible member 101 will be described.

The variable stiffness device 20 is installed in the flexible member 101 without any restriction on the second elongated member 40 and the moving member. For example, the first elongated member 30, the second elongated member 40, and the moving member are arranged with a small space in a limited space in the flexible member 101. The limited space means a space that can just contain the first elongated member 30, the second elongated member 40, and the moving member. Accordingly, even a slight deformation in one of the first elongated member 30 and the second elongated member 40, and the flexible member 101 may provide a contact therebetween to apply an external force to the other. The flexible member 101 need only have a space slightly larger than the first elongated member 30, the second elongated member 40, and the moving member.

For example, the flexible member 101 is a tube having an inner diameter slightly larger than the outer diameter of the variable stiffness device 20, in particular, the outer diameter of the high-bending stiffness portion 31, and is capable of being flexed by application of an external force. The first elongated member 30, the second elongated member 40, and the moving member may be arranged inside the tube. The first elongated member 30 is relatively positioned and fixed to the flexible member 101, and the second elongated member 40 is movable relative to the first elongated member 30 and the flexible member 101. For example, the flexible member 101 may be an insertion section of the endoscope 100. The endoscope 100 may be either for medical purposes or for industrial purposes. Accordingly, as shown in FIG. 1B, the endoscope 100 comprises a flexible member 101 and a variable stiffness device 20 that is installed in the flexible member 101 and provides the flexible member 101 with different degrees of stiffness. The flexible member 101 is an example of a small-sized precision device in which the variable stiffness device 20 is installed. Examples of such a small-sized precision device include a manipulator and an elongated member such as a catheter, as well as the insertion section. The motor and control device 80 of the moving mechanism 60 may be arranged in the endoscope 100 or in a control device (not illustrated) for the endoscope 100 connected to the endoscope 100. Accordingly, the variable stiffness system 10 is arranged in the endoscope 100 or in the endoscope system including the endoscope 100 and the control device for the endoscope 100.

Hereinafter, the variation of the stiffness of a desired area in the flexible member 101 according to the present embodiment will be described.

In the description that follows, a non-heated shape-memory member 41, which is in the first phase and in the low-stiffness state, will be referred to as a "low shape-memory member" for convenience in explanation. Also, a heated shape-memory member 41, which is in the second phase and in the high-stiffness state, will be referred to as a "high shape-memory member" for convenience in explanation. A high shape-memory member is arranged next to a low shape-memory member. In FIGS. 2A, 2B, 2C, and 2D, low shape-memory members are hatched in the same manner as those in FIG. 1A, and high shape-memory members are filled in with black, in order to distinguish between the low shape-memory members and the high shape-memory members.

Let us assume that the variable stiffness system 10 is in an initial state, as shown in FIG. 2A. In the initial state, the switch in the control section 103 is turned off, and the moving mechanism 60 is deactivated. An end of the second elongated member 40 opposite to the moving mechanism 60 projects outward from an end of the first elongated member 30. In association with this projection, the first shape-memory member 41 from the left shown in FIG. 2A, the first soft member 43 from the left shown in FIG. 2A, and an end of the inner support member 45 covering them are arranged outside the first elongated member 30. The second, third, fourth, fifth, and sixth soft members 43 from the left shown in FIG. 2A and the second and fourth shape-memory members 41 from the left shown in FIG. 2A overlap the high-bending stiffness portions 31. The third and fifth shape-memory members 41 from the left shown in FIG. 2A overlap the low-bending stiffness portions 33.

Although not illustrated in the drawings, in the initial state, if a low-bending stiffness portion 33 wounds around the majority of a shape-memory member 41 in the entire length of the shape-memory member 41, and the second elongated member 40 may be contained in the first elongated member 30 over the entire length of the second elongated member 40.

In the initial state, the driver 81 does not supply current to the low-bending stiffness portions 33, and the low-bending stiffness portions 33 do not generate heat; thus, the shape-memory members 41 are not heated and are in the first phase. Accordingly, all the shape-memory members 41 are low shape-memory members, and the first elongated member 30, the second elongated member 40, the shape-memory members 41, and the flexible member 101 are in the low-stiffness state over their entire lengths.

That is, the low shape-memory members overlap the high-bending stiffness portions 31 or the low-bending stiffness portions 33. In other words, the low shape-memory members are covered by the high-bending stiffness portions 31 or the low-bending stiffness portions 33, and are contained in the high-bending stiffness portions 31 or the low-bending stiffness portions 33. Referring to the shape-memory members 41 overlapping the low-bending stiffness portions 33, the shape-memory members 41 are low shape-memory members, and are soft members. Accordingly, the low-bending stiffness portions 33 are in a bendable state.

The low-bending stiffness portions 33 are relatively positioned and fixed to desired areas in the flexible member 101. Accordingly, the desired areas to which the low-bending stiffness portions 33 are fixed are provided with a relatively low stiffness by the overlap between the third and fifth shape-memory members 41 from the left shown in FIG. 2A (low shape-memory members) and the low-bending stiffness portions 33, resulting in a decrease in the stiffness of the desired areas. That is, the variable stiffness device 20 provides only parts of the flexible member 101 in the entire length of the flexible member 101 with a low stiffness. The parts of the flexible member 101 in the low-stiffness state are easily deformed by an external force acting on the flexible member 101. The flexible member 101 becomes easily flexible by an external force. The variable stiffness device 20 and the flexible member 101 become easily bendable.

In addition, since the high-bending stiffness portions 31 are hard portions, the high-bending stiffness portions 31 are capable of maintaining a substantially linear state. Accordingly, parts of the flexible member 101 at which the high-bending stiffness portions 31 are arranged maintain a substantially linear state. The high-bending stiffness portions 31 may be flexed more gently than the low-bending stiffness portions 33 by an external force. Accordingly, parts of the flexible member 101 may be flexed more gently than the desired area by an external force.

Thereafter, the switches in the drivers 81 are turned on, as shown in FIG. 2B, while the switch in the control section 103 remains off, the moving mechanism 60 remains deactivated, and the second elongated member 40 does not move relative to the initial state shown in FIG. 2A. Thereby, the drivers 81 supplies electric currents to the low-bending stiffness portions 33 through the wirings 83. The low-bending stiffness portions 33 generate heat in response to the current supply. The heat is indirectly transferred from the low-bending stiffness portions 33 to the third and fifth shape-memory members 41 from the left shown in FIG. 2B (low shape-memory members in FIG. 2A) through parts of the outer support member 35 in the entire length of the outer support member 35 that the low-bending stiffness portions 33 winds around, and through parts of the inner support member 45 in the entire length of the inner support member 45 that part of the outer support member 35 winds around. That is, the heat is indirectly transferred from the low-bending stiffness portions 33 to the third and fifth shape-memory members 41 from the left shown in FIG. 2B. The heat is not directly transferred from the low-bending stiffness portions 33 to the third and fifth low shape-memory members from the left shown in FIG. 2B.

Through the heat transfer, the third and fifth shape-memory members 41 from the left shown in FIG. 2B (low shape-memory members in FIG. 2A) are heated, and the temperature of the shape-memory members 41 increases. The third and fifth shape-memory members 41 from the left shown in FIG. 2B switch in phase from the first phase to the second phase through being heated, and the shape-memory members 41 increase in stiffness through being heated. Thereby, the third and fifth shape-memory members 41 from the left shown in FIG. 2B switch from the low-stiffness state to the high-stiffness state, and the low shape-memory members shown in FIG. 2A change to high shape-memory members in FIG. 2B. The low-bending stiffness portions 33 cause the third and fifth shape-memory members 41 from the left shown in FIG. 2B (low shape-memory members in FIG. 2A), which overlap the low-bending stiffness portions 33, to transition in phase from the first phase to the second phase. The low-bending stiffness portions 33 vary the third and fifth shape-memory members 41 from the left shown in FIG. 2B, which overlap the low-bending stiffness portions 33, from the low-stiffness state to the high-stiffness state.

Referring to the shape-memory members 41 overlapping the low-bending stiffness portions 33, the shape-memory members 41 are high shape-memory members, and are also hard members. Accordingly, the low-bending stiffness portions 33 are in a hardly bendable state.

For example, the heat transfer from the low-bending stiffness portions 33 to the high-bending stiffness portions 31, and the heat transfer from the high-bending stiffness portions 31 to the inner support member 45 through the outer support member 35 are suppressed by the thermal conductivities of the high-bending stiffness portions 31, the outer support member 35, and the inner support member 45. For example, this suppression suppresses heat transfer from the low-bending stiffness portions 33 to the shape-memory members 41 other than the third and fifth shape-memory members 41 from the left shown in FIG. 2B (see the first, second, and fourth low shape-memory members from the left shown in FIG. 2B) through the high-bending stiffness portions 31, the outer support member 35, and the inner support member 45.

The thermal conductivity of the soft members 43 is lower than the thermal conductivity of the shape-memory members 41. This suppresses heat transfer from the third and fifth shape-memory members 41 from the left shown in FIG. 2B (high shape-memory members), which have been heated, to the second and fourth shape-memory members 41 from the left shown in FIG. 2B (low shape-memory members), which have not been heated, via the soft members 43.

In this manner, when the low-bending stiffness portions 33 that also serve as the inducing members 50 cause the third and fifth shape-memory members 41 from the left shown in FIG. 2B (low shape-memory members in FIG. 2A), arranged in the low-bending stiffness portions 33, to vary in stiffness, the second and fourth shape-memory members 41 from the left shown in FIG. 2B (low shape-memory members in FIG. 2A), arranged next to the third and fifth shape-memory members 41 from the left shown in FIG. 2B (low shape-memory members) to be varied in stiffness are arranged in the high-bending stiffness portions 31. When the third and fifth shape-memory members 41 from the left shown in FIG. 2B are arranged in the low-bending stiffness portions 33 to be varied from the low-stiffness state to the high-stiffness state, the second and fourth shape-memory members 41 from the left shown in FIG. 2B, arranged next to the third and fifth shape-memory members 41 from the left shown in FIG. 2B (low shape-memory members), which are varied from the low-stiffness state to the high-stiffness state, are arranged in the high-bending stiffness portions 31, and are in the low-stiffness state. Specifically, the high shape-memory members are arranged inside the low-bending stiffness portions 33, and the low shape-memory members are arranged inside the high-bending stiffness portions 31.

The low-bending stiffness portions 33 are relatively positioned and fixed to desired areas in the flexible member 101. Accordingly, the desired areas to which the low-bending stiffness portions 33 are fixed are provided with a relatively high stiffness by the overlap between the third and fifth shape-memory members 41 from the left shown in FIG. 2B (high shape-memory members) and the low-bending stiffness portions 33, resulting in an increase in the stiffness of the desired areas. That is, parts of the flexible member 101 at which the low-bending stiffness portions 33 that the third and fifth shape-memory members 41 from the left shown in FIG. 2B (high shape-memory members) overlap are arranged increase in stiffness. In other words, the variable stiffness device 20 provides only parts of the flexible member 101 in the entire length of the flexible member 101 with a high stiffness. Accordingly, the flexible member 101 does not switch from the low-stiffness state to the high-stiffness state over the entire length of the flexible member 101, but partially switches from the low-stiffness state to the high-stiffness state. In other words, parts in the entire length of the flexible member 101 switch from the low-stiffness state to the high-stiffness state. In this manner, the variable stiffness device 20 varies the stiffness state of the variable stiffness device 20 in the low-bending stiffness portions 33, and the stiffness of the variable stiffness device 20 partially increases in the longitudinal axis direction of the variable stiffness device 20. By this variation, the variable stiffness device 20 increases the stiffness of desired areas in the flexible member 101.

Parts of the flexible member 101 in the high-stiffness state resist the external force acting on the flexible member 101, namely, the force capable of deforming the heated shape-memory members 41 (high shape-memory members). Accordingly, parts of the flexible member 101 in the high-stiffness state maintain a substantially linear state. Parts of the flexible member 101 may be flexed gently as compared to the initial state by an external force.

The second and fourth shape-memory members 41 from the left shown in FIG. 2B, which overlap the high-bending stiffness portions 31, remain as low shape-memory members, because heat is not transferred thereto, and are soft members. However, since the high-bending stiffness portions 31 are hard portions, the high-bending stiffness portions 31 are capable of maintaining a substantially linear state, as in the state shown in FIG. 2A. Accordingly, parts of the flexible member 101 at which the high-bending stiffness portions 31 are arranged maintain a substantially linear state. The high-bending stiffness portions 31 may be flexed more gently than the low-bending stiffness portions 33 by an external force. Accordingly, parts of the flexible member 101 may be flexed more gently than the desired area by an external force.

In the present embodiment, for example, the third and fifth shape-memory members 41 from the left shown in FIG. 2B are heated. Accordingly, two parts in the entire length of the flexible member 101 switch from the low-stiffness state to the high-stiffness state. However, only one shape-memory member 41 may be heated.

Let us assume that the third shape-memory member 41 from the left shown in FIG. 2B is fixed to a desired first area in the flexible member 101, and that the fifth shape-memory member 41 from the left shown in FIG. 2B is fixed to a desired second area in the flexible member 101. The current supplied to each of the low-bending stiffness portions 33 may be controlled by the control device 80, and the temperature of the third shape-memory member 41 from the left shown in FIG. 2B, which is to be heated, may be different from the temperature of the fifth shape-memory member 41 from the left shown in FIG. 2B, which is to be heated. Thus, the stiffness of the third shape-memory member 41 from the left shown in FIG. 2B (high shape-memory member) may be different from the stiffness of the fifth shape-memory member 41 from the left shown in FIG. 2B (high shape-memory member). Accordingly, when each of the desired first area and second area in the flexible member 101 switches from the low-stiffness state to the high-stiffness state, the stiffness of the desired first area in the flexible member 101 is different from the stiffness of the desired second area in the flexible member 101. In this manner, the stiffness of the flexible member 101 may be partially varied.

In the present embodiment, two low-bending stiffness portions 33 are arranged. Accordingly, both the number of the parts and the number of the areas are two. The number of the parts and the number of the areas correspond to the number of the low-bending stiffness portions 33.

The high-bending stiffness portions 31, which are hard portions, and the third and fifth shape-memory members 41 (high shape-memory members) from the left shown in FIG. 2B are alternately arranged in the longitudinal axis direction of the variable stiffness device 20. Thereby, the variable stiffness device 20 may be in the high-stiffness state over the entire length, so as to provide the flexible member 101 with a high stiffness over the entire length. The flexible member 101 may maintain a substantially linear state over the entire length. The flexible member 101 may be flexed gently as compared to its initial state over the entire length by an external force.

Next, as shown in FIG. 2C, when the switch in the driver 81 is turned off, the driver 81 stops supplying current to the low-bending stiffness portions 33. When the switch in the control section 103 is turned on, the control device 80 controls the moving mechanism 60, and the moving mechanism 60 moves the second elongated member 40 relative to the first elongated member 30, as shown in FIG. 2C. Thereby, the second elongated member 40 is contained in the first elongated member 30 over the entire length.

At this time, the third and fifth shape-memory members 41 from the left shown in FIG. 2C (high shape-memory members) overlap the high-bending stiffness portions 31 over the entire lengths. That is, the high shape-memory members are covered by the high-bending stiffness portions 31 and contained in the high-bending stiffness portions 31. Moreover, the second and fourth shape-memory members 41 from the left shown in FIG. 2C (low shape-memory members) overlap the low-bending stiffness portions 33 over the majority of the entire lengths. That is, the low shape-memory members are covered by the low-bending stiffness portions 33, and contained in the low-bending stiffness portions 33. In this manner, the positions of the high shape-memory members are shifted from the low-bending stiffness portions 33 to the high-bending stiffness portions 31, and the positions of the low shape-memory members are shifted from the high-bending stiffness portions 31 to the low-bending stiffness portions 33. The movements that cause such a shift are simultaneously performed.

The first shape-memory member 41 from the left shown in FIG. 2C (low shape-memory member) and all the soft members 43 overlap the high-bending stiffness portions 31; however, the configuration is not limited thereto.

Referring to the shape-memory members 41 overlapping the low-bending stiffness portions 33, the shape-memory members 41 are low shape-memory members, and are soft members. Accordingly, the low-bending stiffness portions 33 are in a bendable state.

The low-bending stiffness portions 33 are relatively positioned and fixed to desired areas in the flexible member 101. Accordingly, the desired areas to which the low-bending stiffness portions 33 are fixed are provided with a relatively low stiffness by the overlap between the second and fourth shape-memory members 41 from the left shown in FIG. 2C (low shape-memory members) and the low-bending stiffness portions 33, resulting in a decrease in the stiffness of the desired areas. That is, parts of the flexible member 101 at the low-bending stiffness portions 33 that the second and fourth shape-memory members 41 from the left shown in FIG. 2C (low shape-memory members) overlap decrease in stiffness. Thereafter, the variable stiffness device 20 and the flexible member 101 return to the initial state, and return to the low-stiffness state over the entire lengths. In this manner, the variable stiffness device 20 varies the stiffness state of the variable stiffness device 20 in the low-bending stiffness portions 33, and the stiffness of the variable stiffness device 20 partially decreases in the longitudinal axis direction of the variable stiffness device 20. Through this variation, the variable stiffness device 20 decreases the stiffness of desired areas in the flexible member 101, the flexible member 101 is returned to the initial state, and the flexible member 101 is returned to the low-stiffness state over the entire length.

The flexible member 101 in the low-stiffness state is easily deformed by an external force acting on the flexible member 101. Accordingly, the flexible member 101 is easily flexible by an external force. That is, the variable stiffness device 20 and the flexible member 101 become easily bendable.

Even if the third and fifth shape-memory members 41 from the left shown in FIG. 2C (high shape-memory members) overlap the high-bending stiffness portions 31, the operation of the high-bending stiffness portions 31 to the flexible member 101 is substantially the same as the operation in the state shown in FIG. 2A and the operation in the state shown in FIG. 2B. That is, since the high-bending stiffness portions 31 are hard portions, the high-bending stiffness portions 31 are capable of maintaining a substantially linear state. Accordingly, parts of the flexible member 101 at which the high-bending stiffness portions 31 are arranged maintain a substantially linear state. The bending stiffness of the third and fifth shape-memory members 41 from the left shown in FIG. 2C (high shape-memory members), which overlap the high-bending stiffness portions 31 in FIG. 2C, is higher than the bending stiffness of the shape-memory members 41 (low shape-memory members) that overlap the high-bending stiffness portions 31 in FIGS. 2A and 2B. Accordingly, parts of the flexible member 101 at which the high-bending stiffness portions 31 are arranged reliably maintain a substantially linear state as compared to the state shown in FIGS. 2A and 2B. Parts of the flexible member 101 at which the high-bending stiffness portions 31 are arranged reliably maintain a substantially linear state as compared to the states shown in FIGS. 2A and 2B. The high-bending stiffness portions 31 may be flexed more gently than the low-bending stiffness portions 33 by an external force. Accordingly, parts of the flexible member 101 may be flexed more gently than the desired area by an external force.

Figure 2D:
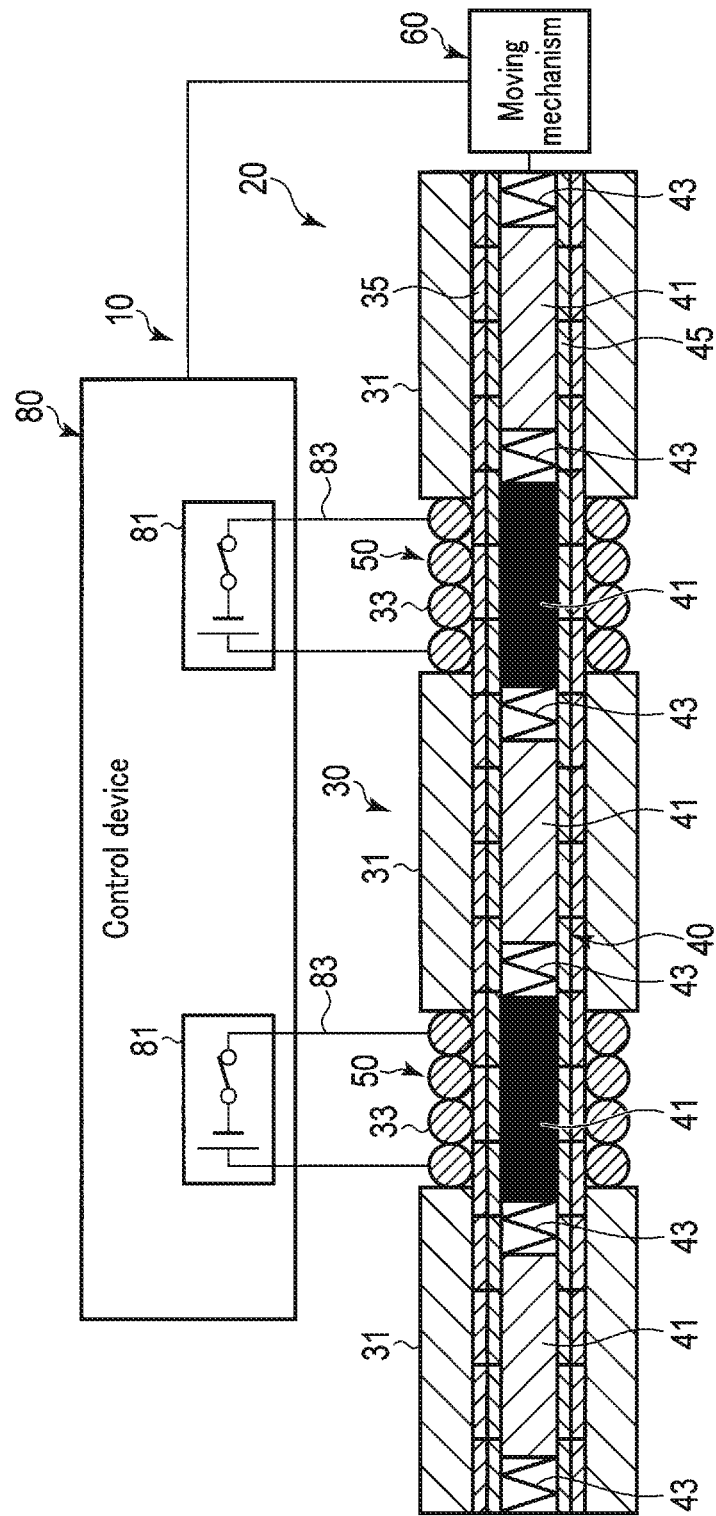
FIG. 2D is a diagram showing that the variable stiffness device shown in FIG. 2C has been switched from the low-stiffness state to the high-stiffness state.

In FIG. 2C, the shape-memory members 41 (low shape-memory members) that overlap the low-bending stiffness portions 33 stand by at the low-bending stiffness portions 33 for switching from the low-stiffness state to the high-stiffness state, as shown in FIG. 2D. As shown in FIGS. 2C and 2D, when the shape-memory members 41 in the low-stiffness state arranged in the low-bending stiffness portions 33 are varied to the high-stiffness state, as shown in FIG. 2C, the shape-memory members 41 in the high-stiffness state are arranged in the high-bending stiffness portions 31. Specifically, when the second and fourth shape-memory members 41 from the left shown in FIG. 2C (low shape-memory members), which have been moved in the low-bending stiffness portions 33 by the moving mechanism 60, are varied from the low-stiffness state to the high-stiffness state by the inducing members 50, as shown in FIG. 2D, the third and fifth shape-memory members 41 from the left shown in FIG. 2C (high shape-memory members), which have already been varied to the high-stiffness state, are arranged in the high-bending stiffness portions 31 by the moving mechanism 60 in FIG. 2C.

Herein, the shape-memory members 41 to be varied from the low-stiffness state to the high-stiffness state are arranged inside the low-bending stiffness portions 33. Specifically, low shape-memory members to be varied to the high-stiffness state from the low-stiffness state are arranged inside the low-bending stiffness portions 33 by the moving mechanism 60. The shape-memory members 41 in the high-stiffness state are arranged inside the high-bending stiffness portions 31. Specifically, the high shape-memory members already varied from the low-stiffness state to the high-stiffness state are arranged inside the high-bending stiffness portion 31 by the moving mechanism 60.

In FIG. 2C, the second elongated member 40 is moved relative to the first elongated member 30, the current supply to the low-bending stiffness portions 33 is stopped, and the variable stiffness device 20 and the flexible member 101 return to the initial state, i.e., to the low-stiffness state over the entire lengths; however, the configuration is not limited thereto. For example, part in the entire length of the flexible member 101 may switch from the high-stiffness state to the low-stiffness state.

For example, let us assume that the second elongated member 40 is not moved relative to the first elongated member 30 from the state shown in FIG. 2B, and that the current supply to the low-bending stiffness portions 33 is not stopped, but is controlled by the control device 80 so as to be reduced relative to the state shown in FIG. 2B. In this case, the temperatures of the third and fifth shape-memory members 41 from the left shown in FIG. 2B, which have been heated, are lower than those in FIG. 2B. The variable stiffness device 20 varies the stiffness state of the variable stiffness device 20 in the low-bending stiffness portions 33, and the stiffness of the variable stiffness device 20 partially decreases in the longitudinal axis direction of the variable stiffness device 20. The flexible member 101 is partially switched from the high-stiffness state to the low-stiffness state. In other words, part in the entire length of the flexible member 101 switches from the high-stiffness state to the low-stiffness state.

When the current is reduced, the amount of current supply to each of the low-bending stiffness portions 33 may be different. Accordingly, when the desired first and second areas in the flexible member 101 are switched from the high-stiffness state to the low-stiffness state, the stiffness of the desired first area in the flexible member 101 may be different from the stiffness of the desired second area in the flexible member 101. In this manner, the stiffness of the flexible member 101 may be partially varied.

Next, as shown in FIG. 2D, when the switches in the driver 81 are turned on, the drivers 81 supply currents to the low-bending stiffness portions 33 through the wirings 83. The low-bending stiffness portions 33 generate heat in response to the current supply. The generated heat is transferred from the low-bending stiffness portions 33 to the second and fourth shape-memory members 41 from the left shown in FIG. 2D (low shape-memory members in FIG. 2C), which overlap the low-bending stiffness portions 33, in a manner similar to FIG. 2B described above. At this time, the moving mechanism 60 remains deactivated, and the second elongated member 40 is not moved from the state shown in FIG. 2C.

Through the heat transfer, the second and fourth shape-memory members 41 from the left shown in FIG. 2D (low shape-memory members in FIG. 2) are heated, and the temperature of the shape-memory members 41 increases, in a manner similar to FIG. 2B described above. Through being heated, the shape-memory members 41 are switched from the first phase to the second phase, and increase in stiffness. This causes the shape-memory members 41 to switch from the low-stiffness state to the high-stiffness state, and the low shape-memory members shown in FIG. 2C change to the high shape-memory members in FIG. 2D.

Referring to the shape-memory members 41 overlapping the low-bending stiffness portions 33, the shape-memory members 41 are high shape-memory members, and are also hard members. Accordingly, the low-bending stiffness portions 33 are in a hardly bendable state.

In a manner similar to FIG. 2B described with reference to FIG. 2B, desired areas to which the low-bending stiffness portions 33 are fixed are provided with a relatively high stiffness by the overlap between the second and fourth shape-memory members 41 from the left shown in FIG. 2D (high shape-memory members) and the low-bending stiffness portions 33, resulting in an increase in the stiffness of the desired areas. In this manner, the variable stiffness device 20 varies the stiffness state of the variable stiffness device 20 in the low-bending stiffness portions 33, and the stiffness of the variable stiffness device 20 partially increases in the longitudinal axis direction of the variable stiffness device 20. By this variation, the variable stiffness device 20 increases the stiffness of desired areas in the flexible member 101.

Moreover, the third and fifth shape-memory members 41 from the left shown in FIG. 2C (high shape-memory members) overlap the high-bending stiffness portions 31. In the course of advancement of stiffness variation in the variable stiffness device from FIG. 2C to FIG. 2D, the third and fifth shape-memory members 41 from the left shown in FIG. 2D are naturally cooled in the high-bending stiffness portions 31. Specifically, the third and fifth shape-memory members 41 from the left shown in FIG. 2D release heat to the outside of the shape-memory members 41, and the released heat advances to the high-bending stiffness portions 31 from the shape-memory members 41 through the inner support member 45 and the outer support member 35, for example. That is, the high-bending stiffness portions 31 receive the heat released from the shape-memory members 41 varied to the high-stiffness state by the heat and arranged in the high-bending stiffness portions 31. The high-bending stiffness portions 31 release the heat to the outside of the variable stiffness device 20. Naturally, the inner support member 45 and the outer support member 35 may release the heat to the outside of the variable stiffness device 20. In this manner, the inner support member 45, the outer support member 35, and the high-bending stiffness portions 31 are used as a transfer path for transferring heat to the outside and a release member for releasing heat to the outside. The temperature of the shape-memory members 41 is lowered by natural cooling, and the shape-memory members 41 switch from the second phase to the first phase. Accordingly, the stiffness of the shape-memory members 41 decreases, and the shape-memory members 41 switch from the high-stiffness state to the low-stiffness state. The shape-memory members 41 overlapping the high-bending stiffness portions 31 can be regarded as soft portions, which have a low stiffness and are easily bendable. That is, the shape-memory members 41 (high shape-memory members) overlapping the high-bending stiffness portions 31 in FIG. 2C stand by at the high-bending stiffness portions 31 for switching from the high-stiffness state to the low-stiffness state, as shown in FIG. 2D.

The natural cooling is performed simultaneously with the heating of the second and fourth shape-memory members 41 from the left shown in FIG. 2D.

When the second and fourth shape-memory members 41 from the left shown in FIGS. 2C and 2D (low shape-memory members) are arranged in the low-bending stiffness portions 33 to be varied from the low-stiffness state to the high-stiffness state, as shown in FIGS. 2C and 2D, the third and fifth shape-memory members 41 from the left shown in FIG. 2C (high shape-memory members) are arranged next to the second and fourth shape-memory members 41 from the left shown in FIG. 2C to be varied from the low-stiffness state to the high-stiffness state. The third and fifth shape-memory members 41 (high shape-memory members) from the left shown in FIG. 2C are arranged in the high-bending stiffness portions 31. As shown in FIG. 2D, the third and fifth shape-memory members 41 from the left are cooled by releasing heat at the high-bending stiffness portions 31, and are varied from the high-stiffness state to the low-stiffness state. The second and fourth shape-memory members 41 (low shape-memory members) from the left shown in FIG. 2C, which are varied from the low-stiffness state to the high-stiffness state, are arranged inside the low-bending stiffness portions 33. The third and fifth shape-memory members 41 (high shape-memory members) from the left shown in FIG. 2C, which are varied from the high-stiffness state to the low-stiffness state by the release of the heat, are arranged inside the high-bending stiffness portions.

In the present embodiment, since the shape-memory members 41 covered by the low-bending stiffness portions 33 are switched in phase between the first phase and the second phase, the stiffness of desired areas in the flexible member 101 can be switched.

In the present embodiment, the shape-memory members 41 in the high-stiffness state are moved from the low-bending stiffness portions 33 to the high-bending stiffness portions 31 by the moving mechanism 60, and the shape-memory members 41 in the low-stiffness state are moved from the high-bending stiffness portions 31 to the low-bending stiffness portions 33 by the moving mechanism 60. That is, it is possible to switch the shape-memory members 41 for the low-bending stiffness portions 33 from the high-stiffness state to the low-stiffness state, in a shorter period of time than the time taken for natural cooling of the shape-memory members 41 in the high-stiffness state, namely, without the need to wait until the temperature of the shape-memory members 41 in the high-stiffness state is lowered. It is thus possible to improve responsiveness to the switching of the stiffness of desired areas in the flexible member 101, and to precisely control the variability of the stiffness. In the present embodiment, the stiffness of the shape-memory members 41 spaced apart from each other, which are arranged in the low-bending stiffness portions 33 spaced apart from each other, is varied by the inducing members 50, respectively. In the present embodiment, the stiffness of a desired area in the flexible member 101 can be varied by varying the stiffness of each of the shape-memory members 41. In the present embodiment, the combination of the first elongated member 30 and the second elongated member 40, and the disposition of the high-bending stiffness portions 31, the low-bending stiffness portions 33, the shape-memory members 41, and the soft members 43 allow a configuration of the variable stiffness device 20 to be simple and thin, resulting in thinning the flexible member 101.

For example, the natural cooling of the third and fifth shape-memory members 41 from the left shown in FIGS. 2C and 2D can be performed simultaneously with the heating of the second and fourth shape-memory members 41 from the left shown in FIGS. 2C and 2D. It is thereby possible to efficiently switch the stiffness of a desired area, and to obtain quick responsiveness at the time of switching the stiffness of a desired area in a short period of time.

In the present embodiment, the inducing members 50 generate heat, which causes the shape-memory members 41 to transition in phase. It is thereby possible in the present embodiment to vary the stiffness of a desired area with a simple configuration.

In the present embodiment, when the temperature of the shape-memory members 41 in a heated high-stiffness state is lowered by natural cooling, and the shape-memory members 41 are returned to the low-stiffness state from the high-stiffness state, the shape-memory members 41 in the high-stiffness state are arranged in the high-bending stiffness portions 31. In the present embodiment, the high-bending stiffness portions 31 can be used as releasing members that release the heat of the shape-memory members 41 to the outside, thereby promoting natural cooling. In addition, a dedicated member or mechanism for cooling can be omitted, and the number of components of the variable stiffness device 20 can be reduced. The high-bending stiffness portions 31 are members configured to provide a relatively high stiffness to the flexible member 101 as hard portions. That is, the high-bending stiffness portions 31 are capable of containing the shape-memory members 41 in the high-stiffness state, releasing the heat, and providing the stiffness. It is thereby possible in the present embodiment to efficiently use the high-bending stiffness portions 31. Only the low-bending stiffness portions 33 serve as the inducing members 50, and the high-bending stiffness portions 31 do not serve as the inducing members 50. Thus, even when the shape-memory members 41 in the high-stiffness state move to the high-bending stiffness portions 31, it is possible to reliably cool the shape-memory members 41 in the high-stiffness state. Moreover, in the present embodiment, the temperature of the shape-memory members 41 in the high-stiffness state can be lowered by natural cooling, without using a dedicated cooling mechanism.

In the present embodiment, the shape-memory members 41 and the soft members 43 can be easily positioned by the inner support member 45, and the lengths of the shape-memory members 41 and the soft members 43 can be easily defined. In the present embodiment, the ease of assembly of the second elongated member 40 can be improved by the inner support member 45. In the present embodiment, the mechanical strength of the second elongated member 40 can be improved by the inner support member 45.

Unlike in the present embodiment, let us assume that the second elongated member 40 does not include the inner support member 45, and that the outer peripheral surfaces of the shape-memory members 41 and the soft members 43 slide on the inner peripheral surface of the outer support member 35. In such a case, the inner and outer peripheral surfaces may be worn away by the sliding. In contrast, it is possible in the present embodiment to prevent wearing caused by moving by the inner support member 45.

In the present embodiment, the low-bending stiffness portions 33 and the high-bending stiffness portions 31 can be easily positioned by the outer support member 35, and the lengths of the high-bending stiffness portions 31 and the low-bending stiffness portions 33 can be easily defined. In the present embodiment, it is possible to improve the ease of assembly of the first elongated member 30 by the outer support member 35. In the present embodiment, it is possible to improve the mechanical strength of the first elongated member 30 by the outer support member 35.

Unlike in the present embodiment, let us assume that the second elongated member 40 does not include the outer support member 35, and that the outer peripheral surface of the inner support member 45 slides on the inner peripheral surfaces of the high-bending stiffness portions 31 and the low-bending stiffness portions 33. The outer and inner peripheral surfaces may be worn away by sliding. In contrast, it is possible in the present embodiment to prevent wearing caused by movement by the outer support member 35.

In the present embodiment, the length of one of the high-bending stiffness portions 31 is longer than the length of one of the low-bending stiffness portions 33. Accordingly, in the present embodiment, the high-bending stiffness portions 31 can contain the shape-memory members 41 (e.g., high shape-memory members) arranged next to the shape-memory members 41 (e.g., low shape-memory members) that overlap the low-bending stiffness portions 33. In the present embodiment, the low shape-memory members can be arranged adjacent to the high shape-memory members, so that two high shape-memory members can be prevented from being arranged continuously in the longitudinal axis direction of the second elongated member 40. It is thereby possible to reliably improve responsiveness to the switching of the stiffness in a desired area.

In the present embodiment, the length of one of the high-bending stiffness portions 31 is longer than the length of one of the shape-memory members 41. Accordingly, in the present embodiment, the high-bending stiffness portion 31 can reliably contain the shape-memory member 41 (low shape-memory member) over the entire length.

In the present embodiment, the sum of the length of one of the high-bending stiffness portions 31 and the length of one of the low-bending stiffness portions 33 is longer than twice the length of one of the shape-memory members 41. Accordingly, in the present embodiment, the high-bending stiffness portions 31 can contain the shape-memory members 41 (e.g., high shape-memory members) arranged next to the shape-memory members 41 (e.g., low shape-memory members) that overlap the low-bending stiffness portions 33. In the present embodiment, the low shape-memory members can be arranged adjacent to the high shape-memory members, so that two high shape-memory members are prevented from being arranged continuously in the longitudinal axis direction of the second elongated member 40. It is thereby possible to reliably improve responsiveness to the switching of the stiffness in a desired area.

In the present embodiment, the thermal conductivity of the soft members 43 is lower than the thermal conductivity of the shape-memory members 41. It is thus possible to suppress heat transfer from the heated shape-memory members 41 (high shape-memory members) to non-heated shape-memory members 41 (low shape-memory members) through the soft members 43. It is thus possible to reliably improve responsiveness to the switching of the stiffness in a desired area.

In the present embodiment, the low-bending stiffness portion 33 also serves as the inducing member 50. Accordingly, it is possible to omit a dedicated member for heating the shape-memory members 41, to reduce the number of parts of the variable stiffness device 20, and to simplify the configuration of the variable stiffness device 20.

In the present embodiment, for example, various members (not illustrated) may be arranged inside the flexible member 101 and outside the first elongated member 30. For example, such members include a light guide member (not illustrated) such as an optical fiber. For example, the light guide member guides the illumination light to the tip of the flexible member 101 in order to emit the illumination light from the tip of the flexible member 101 to the outside of the endoscope 100. In the present embodiment, the second elongated member 40 is moved, and the first elongated member 30 is arranged between the second elongated member 40 and the light guide member (not illustrated). Accordingly, the first elongated member 30 can prevent the wearing down of the second elongated member 40 and the light guide member that could be caused by the movement of the second elongated member 40.

In the present embodiment, the first elongated member 30 is relatively positioned and fixed to the flexible member 101, and the second elongated member 40 is moved by the moving mechanism 60; however, the configuration is not limited thereto. It is only required that one of the first elongated member 30 and the second elongated member 40 be moved by the moving mechanism 60.

In the present embodiment, it is only required that the high-bending stiffness portions 31 and the low-bending stiffness portions 33 be alternately arranged; and the number of the high-bending stiffness portions 31 and the number of the low-bending stiffness portions 33 are not particularly limited. In the present embodiment, it is only required that the shape-memory members 41 and the soft members 43 be alternately arranged; and the number of the shape-memory members 41 and the number of the soft members 43 are not particularly limited.

In the present embodiment, the variable stiffness device 20 also serves as a bidirectional actuator configured to switch the shape of the flexible member 101, as well as the stiffness, when an external force other than gravity is being exerted on the flexible member 101. When an external force other than gravity is not being exerted on the flexible member 101 and the variable stiffness device 20 is in a second state, the variable stiffness device 20 also serves as a unidirectional actuator configured to returns the shape of the flexible member 101 to its original shape.

Figure 3:
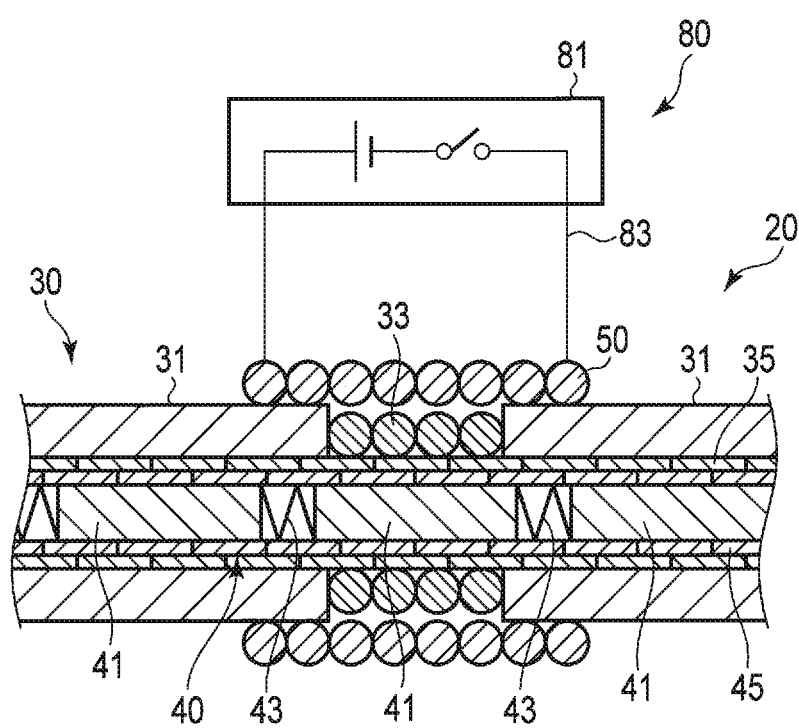
FIG. 3 is a diagram showing an example of a configuration in which a low-bending stiffness portion includes an inducing member.

As an example of a configuration in which the low-bending stiffness portion 33 includes the inducing member 50, the inducing member 50 may be separate from the low-bending stiffness portion 33, as shown in FIG. 3. The inducing members 50 are arranged in the respective low-bending stiffness portions 33.

For example, the inducing member 50 includes a coil member such as a closely wound coil. The coil member of the inducing member 50 may be a loosely wound coil. For example, the inducing member 50 may include a metal, wired, and helical member. For example, the inducing member 50 winds around the outer periphery of the low-bending stiffness portion 33. The inducing member 50 may include a soft tubular member such as a pipe. The inducing member 50 is a cylindrical soft portion having a low bending stiffness. For example, the bending stiffness of the inducing member 50 may be the same as the bending stiffness of the low-bending stiffness portion 33, or different from the bending stiffness of the low-bending stiffness portion 33. The inducing member 50 may surround the entire outer periphery of the low-bending stiffness portion 33.

The inner peripheral surface of the inducing member 50 is separated from the outer peripheral surface of the low-bending stiffness portion 33. The inner peripheral surface of the inducing member 50 may be in close contact with the outer peripheral surface of the low-bending stiffness portion 33. Both ends of the inducing member 50 may surround the outer peripheral surface of the end of the high-bending stiffness portion 31. The inner peripheral surfaces at both ends of the inducing member 50 can be in close contact with the outer peripheral surface at the end of the high-bending stiffness portion 31. That is, the inner peripheral surfaces at both ends of the inducing member 50 may not be in close contact with the outer peripheral surface at the end of the high-bending stiffness portion 31.

The inducing member 50 is electrically connected to the wirings 83. The driver 81 supplies a current to the inducing member 50 through the wirings 83 in response to the ON operation of the switch, and stops supplying the current to the inducing member 50 in response to the OFF operation of the switch. The inducing member 50 transfers the heat to the shape-memory member 41 through the low-bending stiffness portion 33, the outer support member 35, and the inner support member 45. The inducing member 50 serves as a coil heater that is a heating unit configured to heat the shape-memory member 41 through the low-bending stiffness portion 33, the outer support member 35, and the inner support member 45. The inducing member 50 is only required to heat the shape-memory member 41 through the low-bending stiffness portion 33, the outer support member 35, and the inner support member 45, and may be either in or out of direct mechanical contact with the low-bending stiffness portion 33.

[Modifications]

Hereinafter, modifications of the second elongated member 40 according to the present embodiment will be described.

According to a first modification shown in FIG. 4A, the shape-memory member 41 has a tubular, e.g., cylindrical shape. The shape-memory members 41 are not in direct mechanical contact with each other, and are arranged with a desired distance from each other in the longitudinal axis direction of the second elongated member 40. Accordingly, spacing is provided between the shape-memory members 41 in the longitudinal axis direction of the second elongated member 40. The soft member 43 includes a wire that is inserted through each shape-memory member 41. For example, the wire is metallic. The outer peripheral surface of the wire is fixed to the inner peripheral surface of the shape-memory member 41. Accordingly, the shape-memory members 41 and the outer peripheral surfaces of the wire exposed from the shape-memory members 41 are alternately arranged. Such a second elongated member 40 can be easily assembled. In the second elongated member 40 of this modification, the inner support member 45 may be omitted.

Figure 4B:
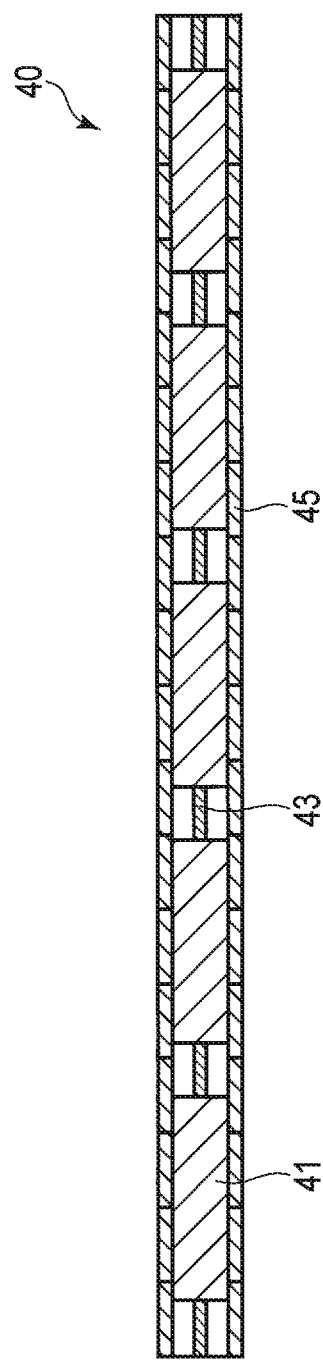
FIG. 4B is a diagram showing a second modification of the second elongated member.

According to a second modification shown in FIG. 4B, the soft members 43 are arranged between the shape-memory members 41, and may include wires connecting the shape-memory members 41. In this case, ends of the connecting wire are fixed to an end of the high-bending stiffness portions 31 adjacent to the ends by bonding or welding, for example. In the second elongated member 40 of this modification, the inner support member 45 may be omitted.

Figure 4C:
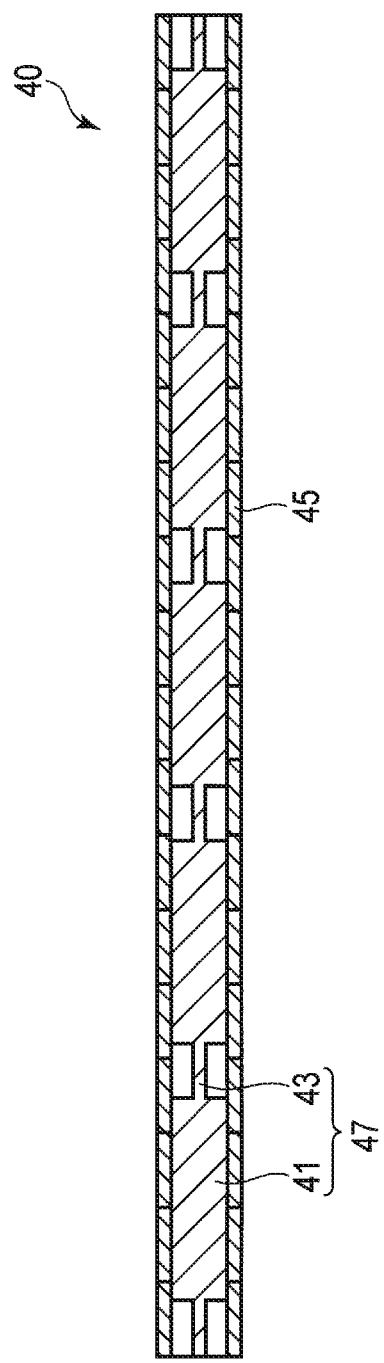
FIG. 4C is a diagram showing a third modification of the second elongated member.

According to a third modification shown in FIG. 4C, the second elongated member 40 may be configured by a linear member 47, which has a linear shape. Similarly to the shape-memory member 41, the linear member 47 includes a member whose phase is transformed according to the temperature, and whose stiffness is greatly varied by the transformation. That is, such a member includes an Ni—Ti-based shape-memory alloy wire or a shape-memory alloy, for example. Processed portions in which the linear member 47 is processed serve as the soft members 43, and portions in which the linear member 47 is not processed serve as the shape-memory members 41. The processing on the portion to be processed may be cutting to reduce the diameter of the linear member 47, or may be forming of a number of abutting grooves extending over the entire periphery. Moreover, the grooves and the cut portions formed in the linear member 47 need not necessarily be formed over the entire periphery of the linear material, and may be formed in a part in the peripheral direction, for example. The soft members 43 are integral with the shape-memory members 41, which are thicker than the soft members 43. In the second elongated member 40 with such a configuration, the assembly of the shape-memory members 41 and the soft members 43 can be omitted. In the second elongated member 40 of this modification, the inner support member 45 may be omitted.

Figure 4D:
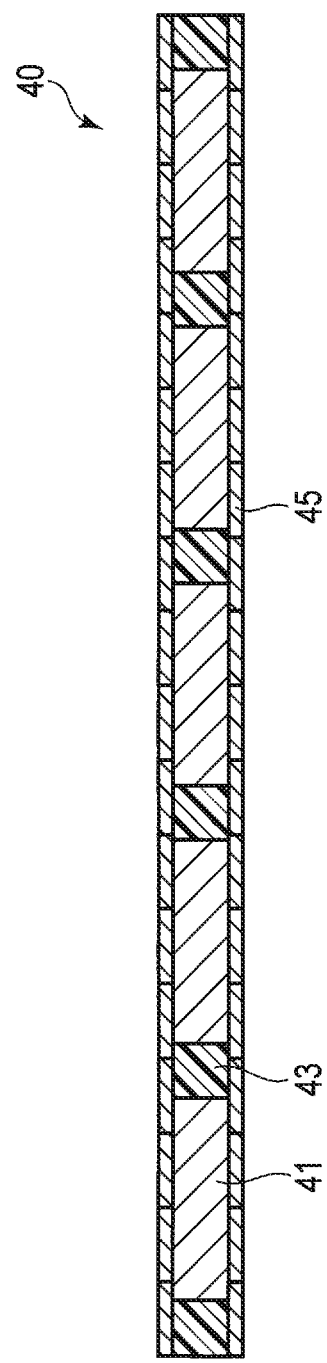
FIG. 4D is a diagram showing a fourth modification of the second elongated member.

According to a fourth modification shown in FIG. 4D, the soft member 43 may have a soft resin material. The thermal conductivity of the resin material is lower than the thermal conductivity of the shape-memory member 41. The resin material may have a pillared shape (e.g., a columnar shape) or a tubular shape (e.g., a cylindrical shape). The thickness of the soft member 43 is substantially the same as the thickness of the shape-memory member 41. It is thereby possible to reliably suppress heat transfer from heated shape-memory members 41 (high shape-memory members) to other non-heated shape-memory members 41 (low shape-memory members) through the soft members 43. Therefore, it is possible to reliably improve responsiveness to the switching of the stiffness in a desired area.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A variable stiffness device comprising:
   a first elongated member including high-bending stiffness portions spaced apart from each other, and at least one low-bending stiffness portion arranged between adjacent high-bending stiffness portions and having a bending stiffness lower than a bending stiffness of the high-bending stiffness portions;
   a second elongated member arranged along the first elongated member and including shape-memory members spaced apart from each other, and at least one connecting member arranged between adjacent shape-memory members;

at least one heater configured to heat at least one of the shape-memory members that is located in the at least one low-bending stiffness portion to increase the bending stiffness of the shape-memory member; and an actuator configured to move the second elongated member relative to the first elongated member, when the heater heats a first shape-memory member of the shape-memory members that is arranged in the low-bending stiffness portion to vary stiffness of the first shape-memory member, a second shape-memory member of the shape-memory members that is arranged next to the first shape-memory member to be varied in stiffness being arranged in a high-bending stiffness portion.

2. The variable stiffness device according to claim 1, wherein, when the first shape-memory member in a low-stiffness state and arranged in the low-bending stiffness portion is varied to a high-stiffness state, the second shape-memory member in a high-stiffness state is arranged in the high-bending stiffness portion.

3. The variable stiffness device according to claim 2, wherein
the high-bending stiffness portions are tubular, and
the second shape-memory member in the high-stiffness state is arranged inside the high-bending stiffness portion.

4. The variable stiffness device according to claim 3, wherein
the low-bending stiffness portion is tubular, and
the first shape-memory member to be varied from the low-stiffness state to the high-stiffness state is arranged inside the low-bending stiffness portion.

5. The variable stiffness device according to claim 4, wherein the second shape-memory member in the high-stiffness state is cooled and varied from the high-stiffness state to the low-stiffness state.

6. The variable stiffness device according to claim 1, wherein
the first shape-memory member has a property of transitioning from the low-stiffness state to the high-stiffness state by heat generated from the heater.

7. The variable stiffness device according to claim 6, wherein the high-bending stiffness portion receives the heat released from the first shape-memory member that has been varied to the high-stiffness state by the heat and then is arranged in the high-bending stiffness portion, and releases the received heat to outside the variable stiffness device.

8. The variable stiffness device according to claim 1, wherein the second elongated member includes an inner supporting member arranged on an outer peripheral side of the shape-memory members and the connecting member, and supporting the shape-memory members and the connecting member.

9. The variable stiffness device according to claim 1, wherein the first elongated member includes an outer supporting member arranged inside the high-bending stiffness portions and the low-bending stiffness portion, and supporting the high-bending stiffness portions and the low-bending stiffness portion.

10. The variable stiffness device according to claim 1, wherein a length of one of the high-bending stiffness portions is longer than a length of the low-bending stiffness portion.

11. The variable stiffness device according to claim 1, wherein a length of one of the high-bending stiffness portions is longer than a length of one of the shape-memory members.

12. The variable stiffness device according to claim 1, wherein a sum of a length of one of the high-bending stiffness portions and a length of the low-bending stiffness portion is longer than twice a length of one of the shape-memory members.

13. The variable stiffness device according to claim 1, wherein a thermal conductivity of the connecting member is lower than a thermal conductivity of the shape-memory members.

14. The variable stiffness device according to claim 1, wherein the low-bending stiffness portion comprises the heater.

15. The variable stiffness device according to claim 1, wherein the low-bending stiffness portion is separate from the heater.

16. The variable stiffness device according to claim 1, wherein
the high-bending stiffness portions are tubular,
the low-bending stiffness portion is tubular, and
when the heater heats the first shape-memory member arranged inside the tubular low-bending stiffness portion to vary stiffness of the first shape-memory member, the second shape-memory member arranged next to the first shape-memory member to be varied in stiffness is arranged inside a tubular high-bending stiffness portion.

17. An endoscope comprising:
a flexible member; and
the variable stiffness device according to claim 1, installed in the flexible member, and configured to provide the flexible member with different degrees of stiffness.

18. The variable stiffness device according to claim 1, wherein the actuator is a motor.

19. A method of varying stiffness of a variable stiffness device,
the variable stiffness device including:
a first elongated member including high-bending stiffness portions spaced apart from each other, and at least one low-bending stiffness portion arranged between adjacent high-bending stiffness portions and having a bending stiffness lower than a bending stiffness of the high-bending stiffness portions;
a second elongated member arranged along the first elongated member, and including shape-memory members spaced apart from each other, and at least one connecting member arranged between shape-memory members, the shape-memory members varying from a first phase to a second phase through being heated, and varying from the second phase to the first phase through being cooled, the shape-memory members having a higher stiffness in the second phase than in the first phase; and
an actuator configured to move the second elongated member relative to the first elongated member,
the method comprising:
heating a first shape-memory member arranged in the low-bending stiffness portion to cause the first shape-memory member to transition to the second phase; and
performing at least one of: maintaining a second shape-memory member arranged next to the first shape-memory member in the first phase, and cooling the second shape-memory member in the second phase.

20. The method of varying the stiffness of the variable stiffness device according to claim 19, further comprising:
- after causing the first shape-memory member to transition to the second phase, causing the actuator to move the second shape-memory member in the low-bending stiffness portion, and then causing the second shape-memory member to transition to the second phase by heating; and
- causing the actuator to move the first shape-memory member next to the second shape-memory member that has been moved in the low-bending stiffness portion, so as to cool the first shape-memory member.

* * * * *